(12) United States Patent
Sigrist

(10) Patent No.: US 7,585,678 B2
(45) Date of Patent: Sep. 8, 2009

(54) METHOD AND APPARATUS FOR POSITIONING A PIPETTING DEVICE

(75) Inventor: Rolf Sigrist, Vitznau (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 555 days.

(21) Appl. No.: 11/524,008

(22) Filed: Sep. 20, 2006

(65) Prior Publication Data
US 2007/0065945 A1    Mar. 22, 2007

(30) Foreign Application Priority Data
Sep. 21, 2005   (EP)   ................................. 05077157

(51) Int. Cl.
*G01N 35/02* (2006.01)
(52) U.S. Cl. .............................. 436/47; 436/43; 436/55; 436/180; 422/64; 422/63; 422/65; 422/100
(58) Field of Classification Search .................. 436/43, 436/47, 55, 180; 422/63–65, 100
See application file for complete search history.

(56) References Cited
U.S. PATENT DOCUMENTS

| | | | | |
|---|---|---|---|---|
| 4,451,433 A | * | 5/1984 | Yamashita et al. ............ | 422/63 |
| 5,270,210 A | * | 12/1993 | Weyrauch et al. ............. | 436/43 |
| 5,270,211 A | * | 12/1993 | Kelln et al. .................... | 436/43 |
| 5,314,825 A | * | 5/1994 | Weyrauch et al. ............. | 436/43 |
| 5,443,791 A | | 8/1995 | Cathcart et al. | |
| 5,529,754 A | | 6/1996 | Bonacina et al. | |
| 5,605,665 A | * | 2/1997 | Clark et al. ................. | 422/102 |
| 6,190,617 B1 | * | 2/2001 | Clark et al. ................. | 422/104 |
| 6,413,475 B2 | * | 7/2002 | Ishizawa et al. ............. | 422/106 |
| 6,945,129 B2 | * | 9/2005 | Escal ....................... | 73/864.24 |
| 7,384,600 B2 | * | 6/2008 | Burns et al. .................. | 422/64 |
| 7,425,303 B2 | * | 9/2008 | Ishizawa et al. .............. | 422/63 |
| 2007/0224083 A1 | * | 9/2007 | Ouchi et al. .................. | 422/64 |

FOREIGN PATENT DOCUMENTS

EP        1 348 966 A2    10/2003
WO    WO 2004/003219 A2    1/2004

* cited by examiner

*Primary Examiner*—Brian R. Gordon
(74) *Attorney, Agent, or Firm*—Marilyn L. Amick; Roche Diagnostics Operations, Inc.

(57) ABSTRACT

A method for determining a reference position for a pipetting needle which is part of an automatic analytical apparatus that includes a rotatable conveyor, conveyor driving means, an automatic pipetting unit having a needle transport device, excenter mechanism, a level detection means, and a reference member for determining a reference position.

2 Claims, 22 Drawing Sheets

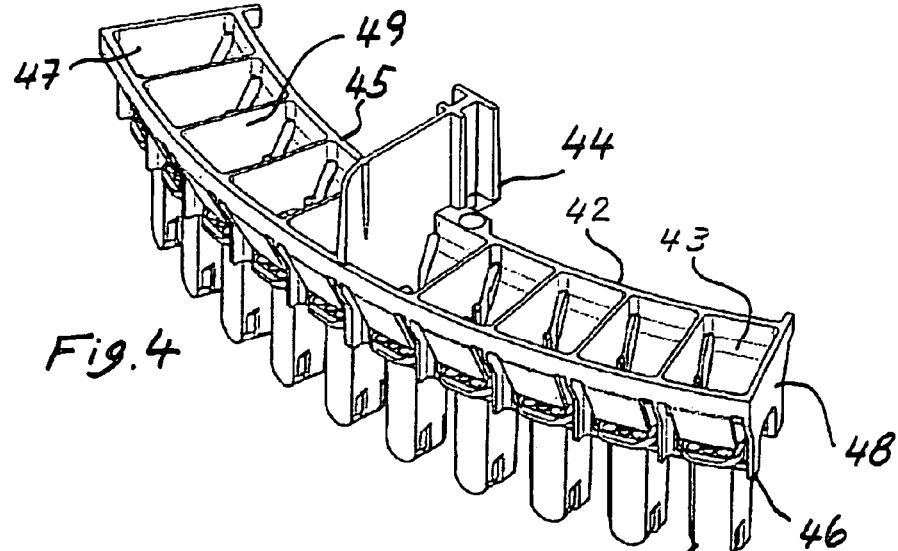
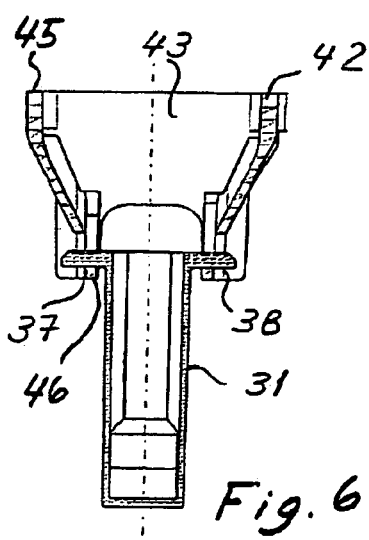
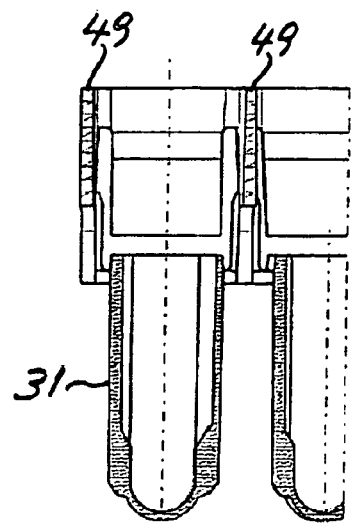
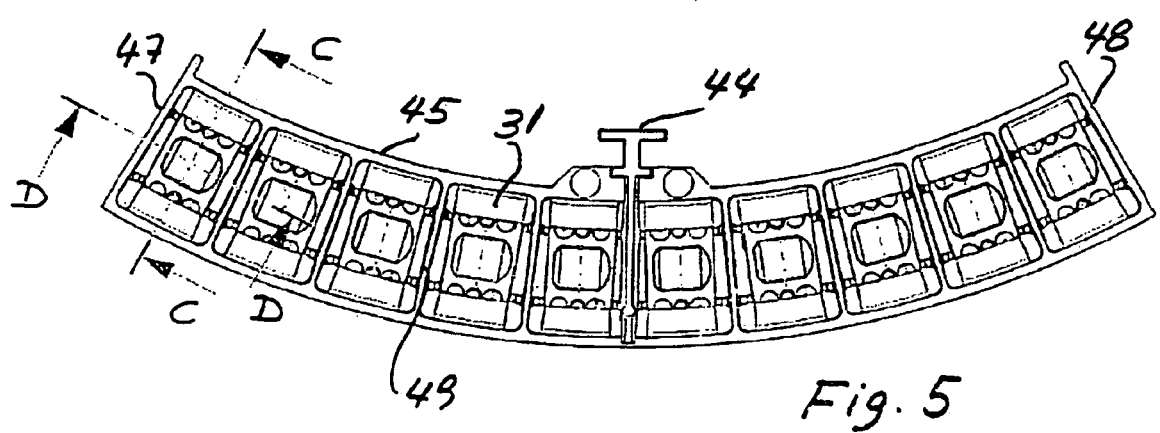

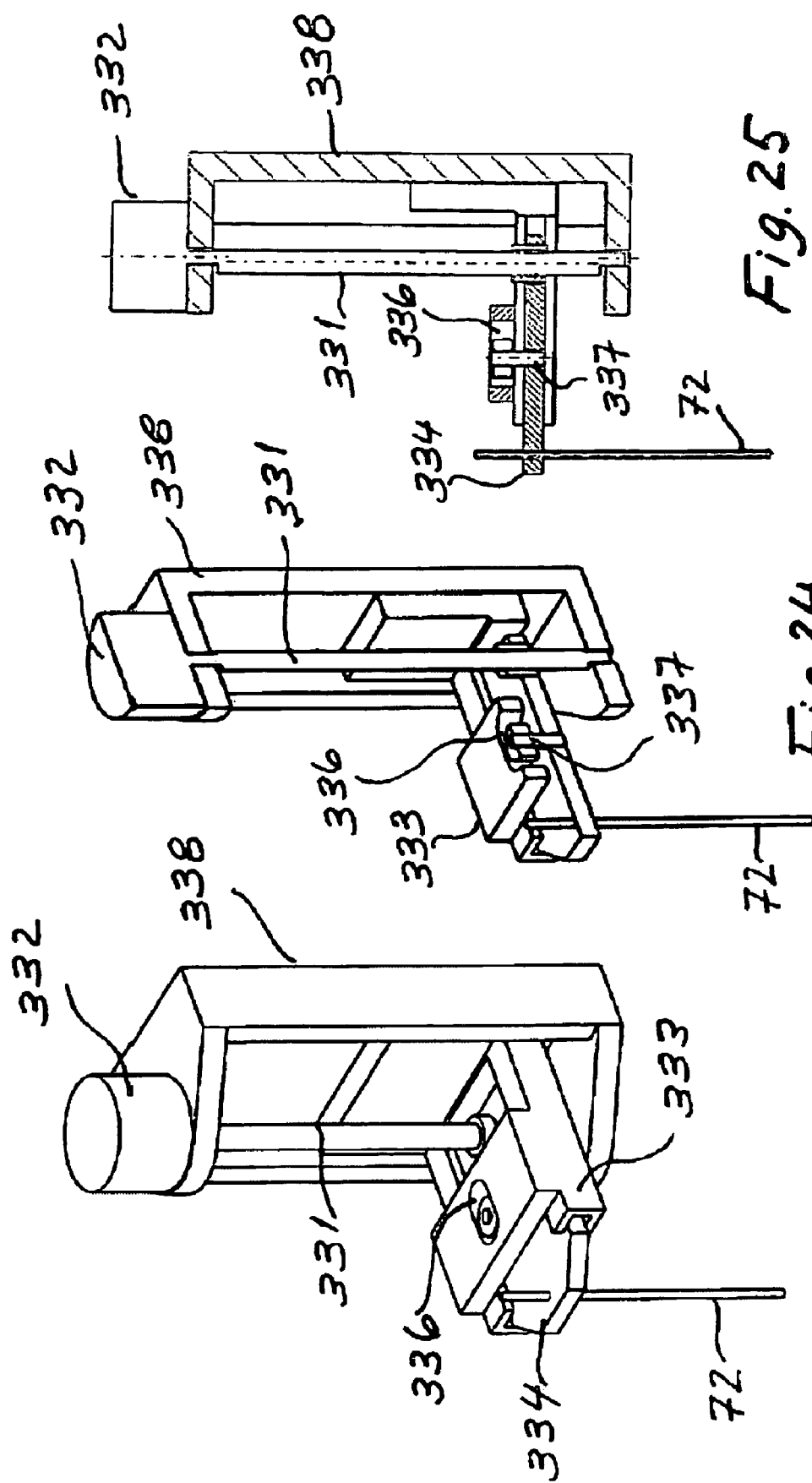

METHOD AND APPARATUS FOR POSITIONING A PIPETTING DEVICE

RELATED APPLICATIONS

This application claims priority to EP 05077157.5 filed Sep. 21, 2005.

FIELD OF THE INVENTION

The invention concerns a method according to the preamble of claim 1. The invention further concerns an analyzer that comprises means for carrying out the method according to the invention.

BACKGROUND

Automatic analyzers, and in particular clinical chemistry analyzers, comprise an automatic pipetting unit with which pipetting operations are performed in a plurality of fixed positions. Even after thorough mechanical adjustment of the position of the pipetting needle during manufacture of the analyzer, the sum of the manufacturing tolerances of the various components of the analyzer and the deformations of the needle with time cause deviations of the position of the pipetting needle and make it difficult to have the pipetting needle properly aligned with the fixed pipetting positions it is expected to be positioned at by a transport device of the automatic pipetting unit. In order to have the pipetting needle properly aligned with the fixed pipetting positions, the operation of the analyzer has to include an initialization process which is carried out at each start of operation of the analyzer and which is suitable for positioning the pipetting needle at a reference, initial or home position, which in a Cartesian system is designated by the coordinates $X_0$, $Y_0$ and $Z_0$ of the tip of the pipetting needle, and which is also called the zero position of the pipetting needle. Once the latter reference position is determined, the transport system of the pipetting needle should be able to position the needle accurately at each pipetting position.

In particular in compact analyzers, where the pipetting needle has to be introduced in vessels which have a relatively small cross-section, and where the distance between pipetting positions is relatively large, it is highly desirable to have a reliable initialization process of the above mentioned kind.

The task of providing such a reliable initialization process is particularly difficult when the transport device moves the pipetting needle only along a straight line, e.g. in X-direction only, and all pipetting positions are located in that linear path of the motion of the pipetting needle. A reliable initialization process is even more difficult to achieve when the portion of the pipetting needle which is introduced into a vessel for effecting a pipetting operation is moved along a circular path within the vessel for mixing liquids introduced in that vessel. In the latter case, a very accurate alignment of the pipetting needle and the vessel is required.

Known initialization methods require relatively expensive means. It is therefore desirable to have an initialization method which is reliable, even under the above mentioned circumstances, and which can be achieved at low cost.

SUMMARY OF THE INVENTION

A first aim of the invention is to provide a method for determining a reference position for a pipetting needle which is part of an automatic analytical apparatus which comprises a rotatable conveyor for conveying reaction cuvettes along a circular path, conveyor driving means for rotating said conveyor in a step-wise manner, an automatic pipetting unit having a pipetting needle for pipetting samples and reagents into said reaction cuvettes, thereby forming liquid sample-reagent-mixtures, said automatic pipetting unit having a needle transport device for moving said pipetting needle along a straight line in a first direction (X-axis) to a plurality of pipetting positions all of which have centers that lie in one and the same vertical plane (X-Z-plane) which passes through said straight line, said needle transport device comprising an excenter mechanism for moving said pipetting needle along a circular path and keeping the length axis of said needle parallel to a vertical axis, level detection means for detecting contact of said pipetting needle with a liquid surface in a vessel or with a metallic part of the apparatus, and a reference member for determining a reference position, said method comprising:

(a) a first measuring step for measuring a first displacement error ($\Delta X$) in a displacement of said pipetting needle effected by said transport device along said straight line in said first direction (X-axis), said first error ($\Delta X$) being caused by a corresponding first angular error ($\phi$) of an initial angular position of said pipetting needle along said circular path determined by said excenter mechanism, said first measuring step comprising actuating the excenter mechanism of the pipette needle to bring the needle in contact with the reference member, (b) a first correcting step for correcting said first displacement error ($\Delta X$) by means of a corresponding correction of said angular error ($\phi$) of said initial angular position of said pipetting needle, (c) a second measuring step for measuring a second displacement error ($\Delta Y$) in a displacement of said pipetting needle in a second direction (Y-axis) perpendicular to said vertical plane, said second displacement error ($\Delta Y$) being caused by a corresponding second angular error ($\alpha$) of an initial angular position of said pipetting needle along said circular path determined by said excenter mechanism, said second measuring step comprising actuating the excenter mechanism of the pipette needle to bring the needle in contact with the reference member, (d) a second correcting step for correcting said second displacement error ($\Delta Y$) by means of a corresponding change ($\alpha$) of the angular position of said pipetting needle along said circular path, (e) a third measuring step for determining the position of a vertical reference line, said reference line being a line where said pipetting needle contacts a fixed first reference plane surface in the apparatus, said first plane surface lying in a plane (Y-Z) perpendicular to said straight line in said first direction (X-axis), and (f) a fourth measuring step for determining the position of a reference point ((X0, Y0, Z0) along said reference line, said reference point being the point where the tip of said pipetting needle contacts a fixed second reference plane surface in the apparatus, said second reference plane surface lying in a plane (X-Z) perpendicular to said reference line.

A second aim of the invention is to provide an analyzer which comprises means for carrying out the method according to the invention. According to a second aspect of the invention the above mentioned third aim is achieved by means of an analyzer comprising:

a rotatable conveyor for conveying reaction cuvettes along a circular path,
   conveyor driving means for rotating said conveyor in a step-wise manner,
   an automatic pipetting unit having a pipetting needle for pipetting samples and reagents into said reaction cuvettes, thereby forming liquid sample-reagent-mixtures,
   said automatic pipetting unit having a needle transport device for moving said pipetting needle along a straight line to a plurality of pipetting positions all of which have centers that lie in one and the same vertical plane which passes through said straight line, and
   said needle transport device comprising an excenter mechanism for moving said pipetting needle along a circular path, keeping the length axis of said needle parallel to a vertical axis,
   level detection means for detecting contact of said pipetting needle with a liquid surface in a vessel or with a metallic part of the apparatus,
   a reference member for determining a reference position for the pipetting needle and for positioning the pipetting needle in said reference position by a method according to claim 1, and
   electronic circuit means for controlling the operation of said conveyor driving means, said needle transport device, said level detection means and said means for determining a reference position for the pipetting needle and for positioning the pipetting needle in said reference position.

A third aim of the invention is to provide a method of use of an analyzer which comprises means for carrying out the method according to the invention. According to a third aspect of the invention the above mentioned third aim is achieved by means of a method of use wherein after positioning of the pipetting needle in said reference position by a method according to claim 1 the angular position of the conveyor is modified to take into account changes in the position of said pipetting needle with respect to the position of a reaction cuvette on said conveyor, said changes being introduced when carrying out said method according to claim 1,
   said modification of the angular position of said conveyor being a change (δ) of the angular position of the conveyor, said change (δ) being calculated taking into account said first displacement error (ΔX) and said second displacement error (ΔY).

The main advantage obtained with a method and an apparatus according to the invention is that it makes possible to (a) achieve a reliable initialization method at low cost, because it uses means available in the analyzer for other purposes, namely an excenter mechanism primarily used for performing mixing of liquids by moving the pipetting needle along a circular path, and level detection means which are primarily used for detecting contact of the pipetting needle with a liquid surface during pipetting operations, and to (b) accurately position a pipetting needle in a plurality of pipetting positions.

BRIEF DESCRIPTION OF THE DRAWINGS

The subject invention will now be described in terms of its preferred embodiments with reference to the accompanying drawings. These embodiments are set forth to aid the understanding of the invention, but are not to be construed as limiting.

FIG. 4 shows a perspective view of a cuvette array according to the invention comprising a cuvette holder 41 and a plurality of cuvettes 31 of the type shown in FIGS. 8-10.

FIG. 5 shows a top plan view of the cuvette array shown in FIG. 4.

FIG. 6 shows a cross-sectional view taken along a plane C-C in FIG. 5 of a chamber of cuvette holder 41 and of a cuvette 31 held by that chamber.

FIG. 7 shows a cross-sectional view taken along a plane D-D in FIG. 5 of a chamber of cuvette holder 41 and of a cuvette 31 held by that chamber.

FIG. 23 shows a schematic perspective view of the structure shown in FIG. 22 suitable for explaining the operation of this structure.

FIG. 24 shows a schematic partial cross-sectional view of the structure shown by FIG. 23.

FIG. 25 shows a cross-sectional view of the structure shown by FIG. 23.

Figure 15:
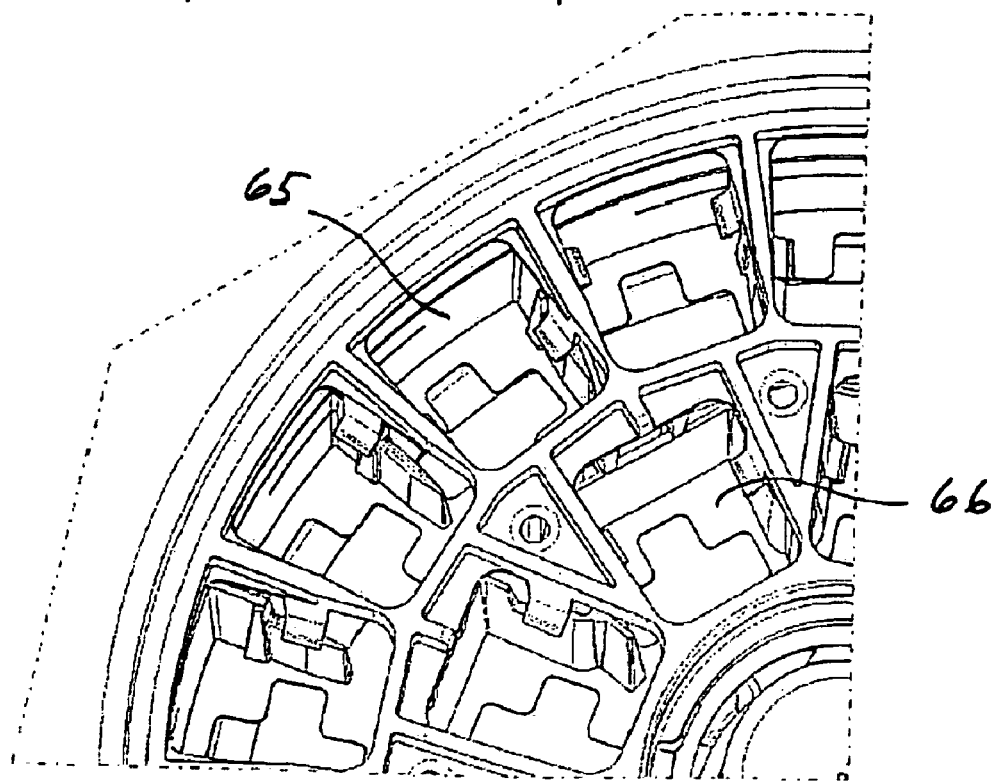
FIG. 15 shows an enlarged view of a portion of FIG. 15.
Figures 17, 18:
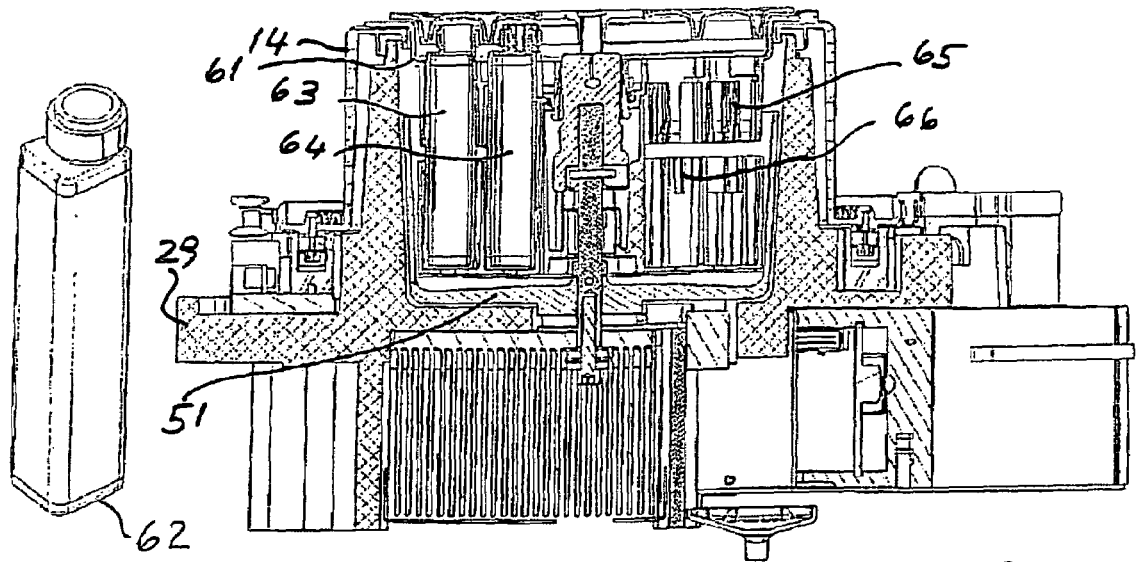
FIG. 17 shows a perspective view of a single reagent container.
FIG. 18 shows a cross-sectional view taken along a plane I-I in FIG. 17.
Figure 19:
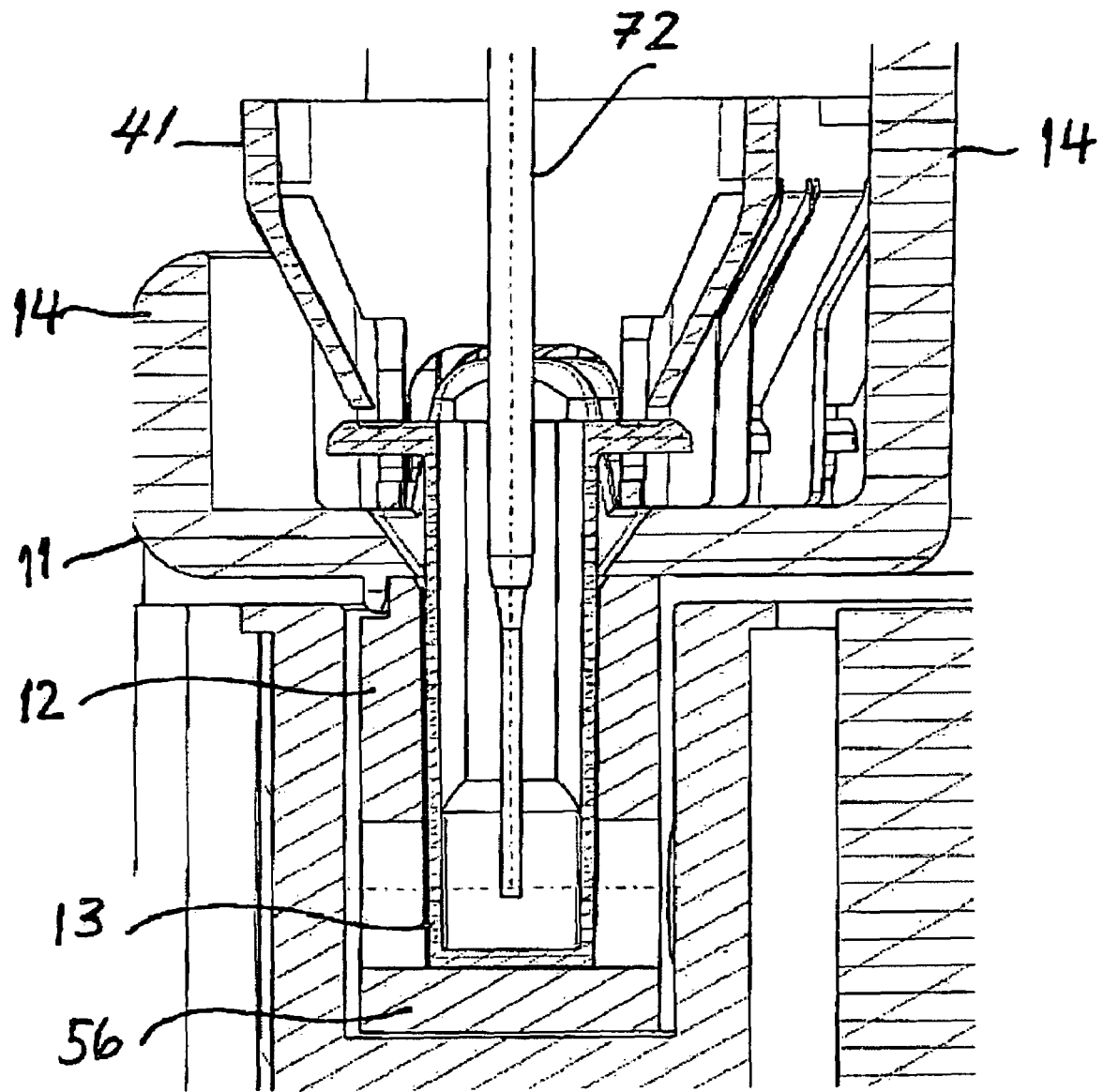
FIG. 19 shows a cross-sectional view of a reaction cuvette 31 and of a pipetting needle 72 positioned therein.
Figure 27:
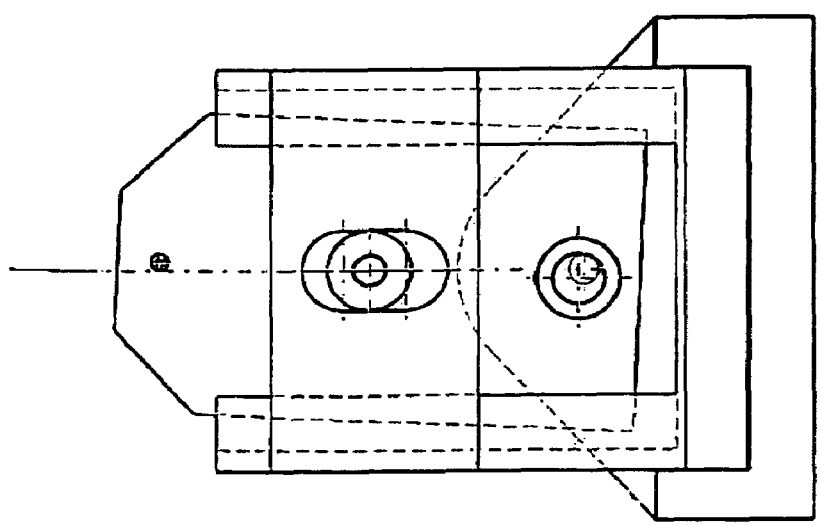
FIG. 27 shows a schematic top view of the structure shown by FIG. 23 connecting plate 334 in a second position, with pipetting needle outside of the symmetry axis 342 of guide 333.
Figure 28:
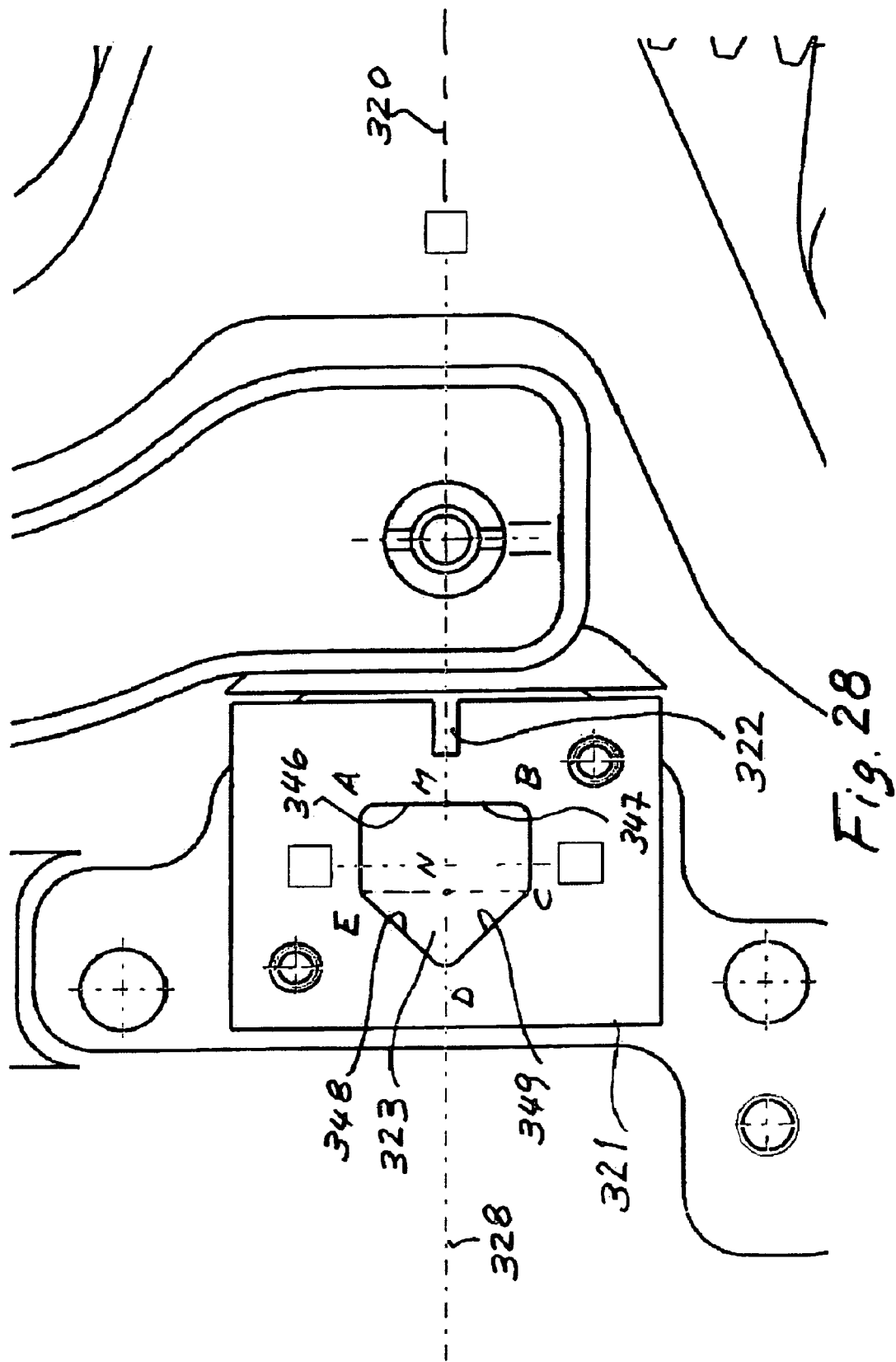
FIG. 28 shows a top view of reference member 321 in FIG. 1.
Figure 29:
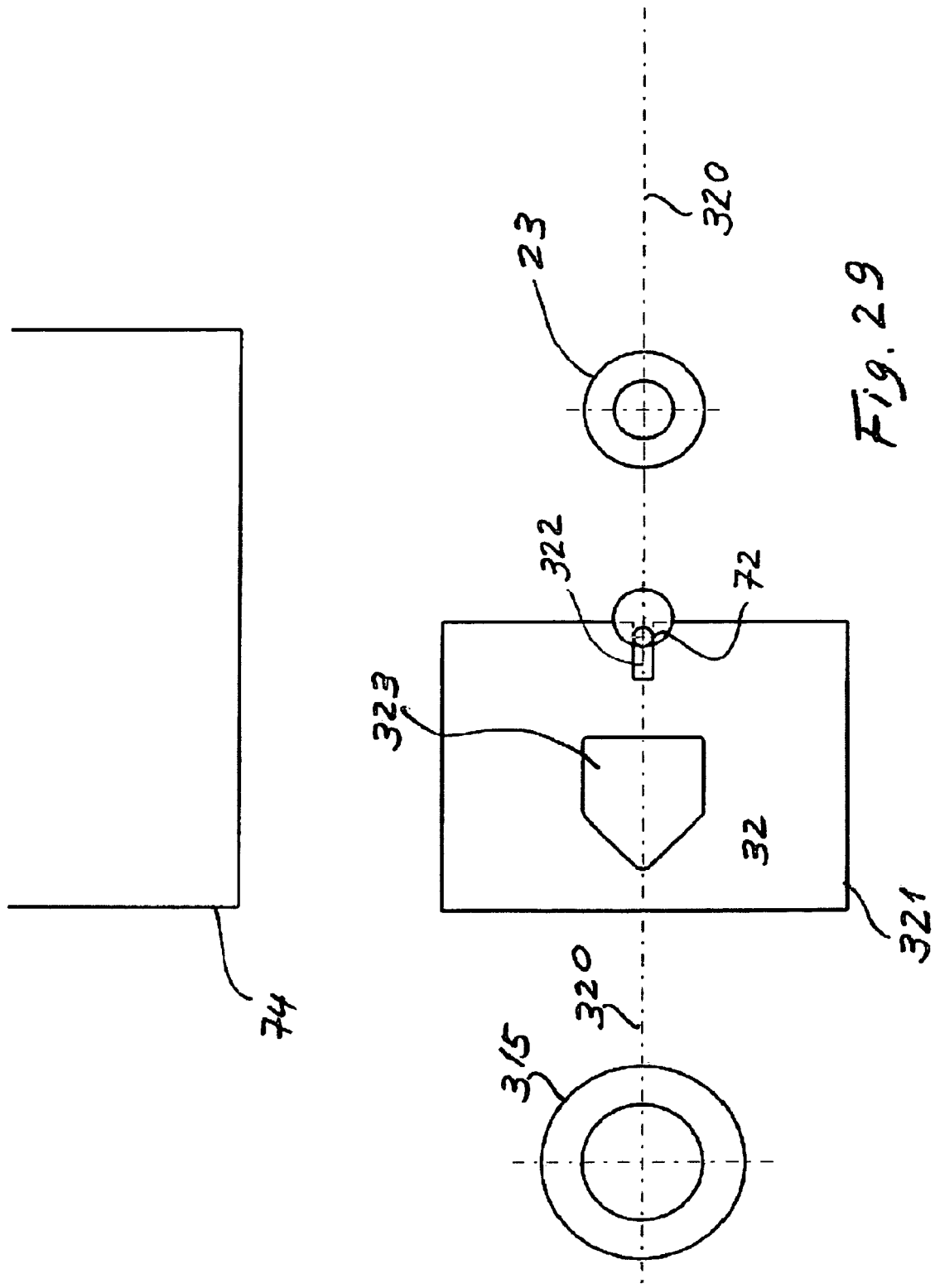
FIG. 29 illustrates the step of rough mechanical adjustment of the position of the pipetting needle in the analyzer.

REFERENCE NUMERALS IN DRAWINGS 11 conveyor
12 first ring shaped body
13 cavity for receiving a reaction cuvette
14 second ring shaped body
15 wall of second ring shaped body
16 opening
17 first chamber (within second ring shaped body)
18 sample tube area
19 cavity for receiving a sample tube
20 thermal block
21 photometer
22 rotor driving means
23 washing station
24 path of light beam of photometer
25 rotation axis of conveyor 11
26 portion of FIG. 15
27 portion of FIG. 17
28 portion of FIG. 19
29 thermal insulation layer
31 reaction cuvette
32 body of cuvette 31
33 lower end portion of cuvette 31
34 upper end portion of cuvette 31
35 bottom wall of cuvette 31
36 opening of cuvette 31
37 tongue
38 tongue
39 length symmetry axis of cuvette 31
40 tongue
41 cuvette holder
42 body of cuvette holder
43 chamber of cuvette holder
44 connecting part/guiding rib
45 upper frame
46 lower frame
47 side wall
48 side wall
49 intermediate wall
50 tongue
51 bucket/hollow body
52 bottom wall of bucket
53 side walls of bucket
54 second chamber within bucket
55 air gap
56 bottom wall of cavity 13
57 depression in inner surface of bottom wall 56
58 edge
59 edge
60 intermediate wall
60a intermediate wall
61 reagent container assembly
62 reagent container
63 reagent container
64 reagent container
65 chamber for receiving a reagent container
66 chamber for receiving a reagent container
71 automatic pipetting device
72 pipetting needle
73 rail of transport device of pipetting needle
74 transport head for transporting pipetting needle 72
312 first opening for pipetting reagents
313 second opening for pipetting reagents
314 opening for pipetting into reaction cuvettes
315 opening for pipetting into chamber of an ISE device
316 cover part
317 cover part
318 cover part
319 opening giving access to reference member 321
320 pipetting axis
321 reference member for initialization process
322 opening on one side of reference member 321
323 opening in the central part of reference member 321
324 limit stop
325 limit stop
328 symmetry axis of opening 323
331 excenter shaft
332 excenter motor
333 guide
334 connecting plate
335 connecting piece
336 elongated opening of guide 333
337 ball bearing pin 338 frame part
339 bushing
341 rotation axis of excenter shaft 331
342 symmetry axis of guide 333
343 arrow indicating the sense of rotation of excenter shaft 331
344 arrow indicating the sense of the motion of needle 72 along a circular path
345 inner side surface of opening 323
346 inner side surface of opening 323
347 inner side surface of opening 323
348 inner side surface of opening 323
349 inner side surface of opening 323
351 theoretical cuvette axis
352 corrected cuvette axis
353 center of circular path of pipetting needle 72
361 circular path of needle 72
362 circular path of needle 72
363 circular path of needle 72
364 circular path of needle 72
365 circular path of needle 72
366 circular path of needle 72
372 circular path of pipetting needle 72
373 position of pipetting needle 72 after correction of angular position of conveyor with correction angle δ
374 position of circular path 372 after correction of angular position of conveyor with correction angle δ
381 schematic representation of excenter which moves needle 72 along a circular path
382 inner radius of washing station
383 outer radius of washing station

DETAILED DESCRIPTION OF THE INVENTION

Preferred embodiments are described hereinafter with reference to the accompanying drawings.

Example of an Analyzer

Figure 1:
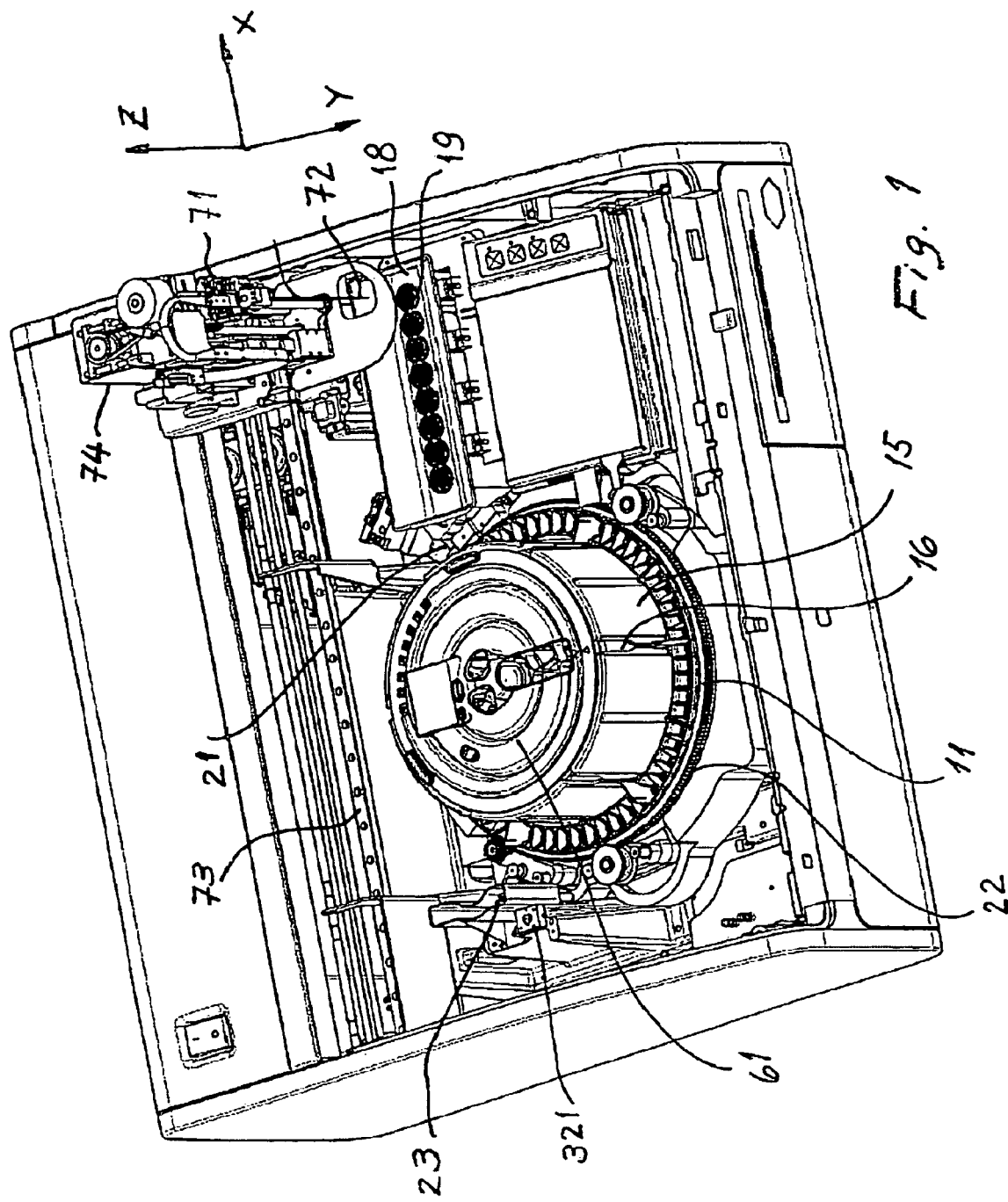
FIG. 1 shows a perspective view of an analyzer according to the invention.

As shown by FIG. 1 an analyzer according to the invention, e.g. a clinical-chemistry for analyzing sample-reagent mixtures contained in reaction cuvettes. The analyzer shown in FIG. 1 comprises a rotatable conveyor 11 for conveying reaction cuvettes 31 inserted in corresponding cavities of that conveyor along a circular path, at least one array of reaction cuvettes 31, a hollow body 51 (shown in FIG. 14) arranged in the central part of conveyor, a reagent container assembly 61 installed in a cavity 54 of hollow body 51, a sample tube area 18 located adjacent to conveyor 11, an automatic pipetting unit 71, a photometer 21 located adjacent to conveyor 11, and conveyor driving means 22 for rotating conveyor 11.

Figure 3:
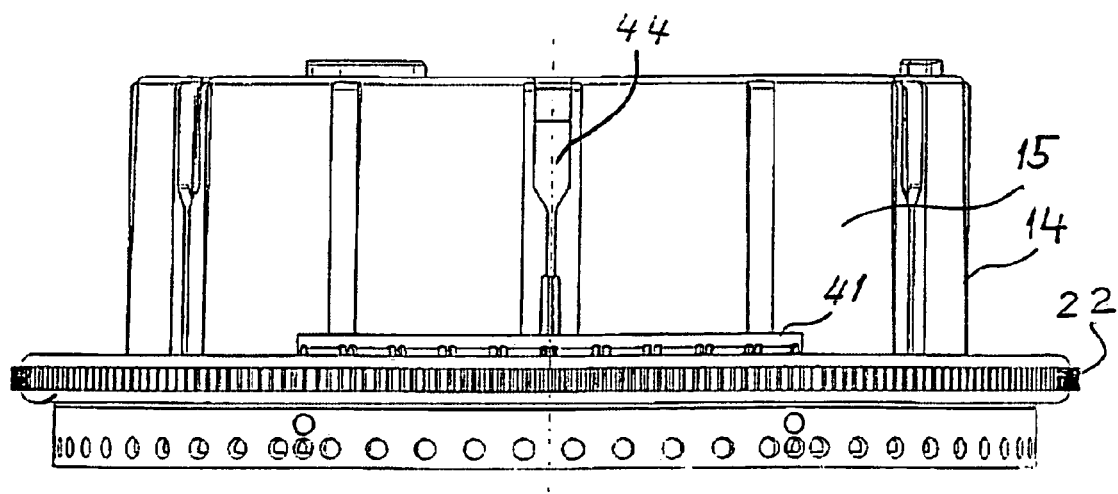
FIG. 3 shows a side view of conveyor 11 in FIG. 1.

FIG. 3 shows the rotation axis 25 of conveyor 11.

Reaction cuvettes 31 inserted in the above mentioned cavities of conveyor 11 are loosely held by a cuvette holder 41 described hereinafter in particular with reference to FIGS. 4 to 7. Such a cuvette holder 41 loosely holds a plurality of reaction cuvettes 31. A cuvette holder 41 and reaction cuvettes 31 held by cuvette holder 41 form a cuvette array. The analyzer comprises at least one such array. Usually reaction cuvettes of a plurality of such cuvette arrays are installed in corresponding cavities of conveyor 11. In the example shown by FIG. 1, conveyor 11 has cavities for receiving 60 reaction cuvettes distributed in 6 cuvette arrays each array having 10 reaction cuvettes.

Figure 2:
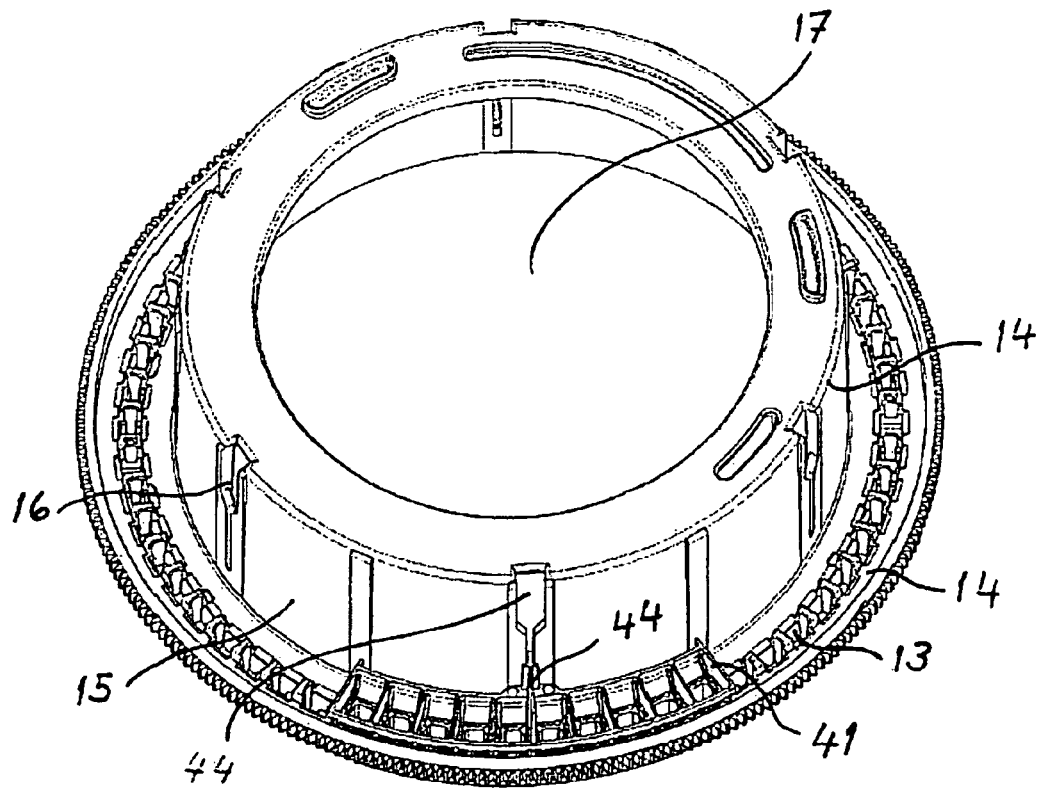
FIG. 2 shows a perspective view of conveyor 11 in FIG. 1.

Cuvette holder 41 serves for holding an array of reaction cuvettes 31. Cuvette holder 41 has a connecting part 44 which is adapted for inserting it into an opening 16 of wall 15 of the conveyor, thereby connecting cuvette holder 41 to conveyor 11. As shown by FIG. 2, the relative position of the connecting part 44 and the opening 16 of wall 15 are such that when connecting part 44 is inserted into opening 16 the reaction cuvettes 31 held by a cuvette holder 41 are inserted into corresponding cavities 13 of a first ring shaped body 12 of conveyor 11.

As shown by FIGS. 2 and 3, conveyor 11 comprises a first ring shaped body 12 and a second ring shaped body 14. First ring shaped body 12 has a circular array of cavities 13, each of which is adapted for receiving a single reaction cuvette 31 of the type described below with reference to FIGS. 8 to 10. First ring shaped body 12 is preferably made of a suitable metal.

Second ring shaped body 14 has a wall 15 which extends upwardly from the inner side of first ring shaped body 12. Wall 15 has openings 16, each of which is adapted for receiving a corresponding connecting part 44 of a cuvette holder 41. Second ring shaped body 14 defines a chamber 17 within the interior of body 14.

Figure 13:
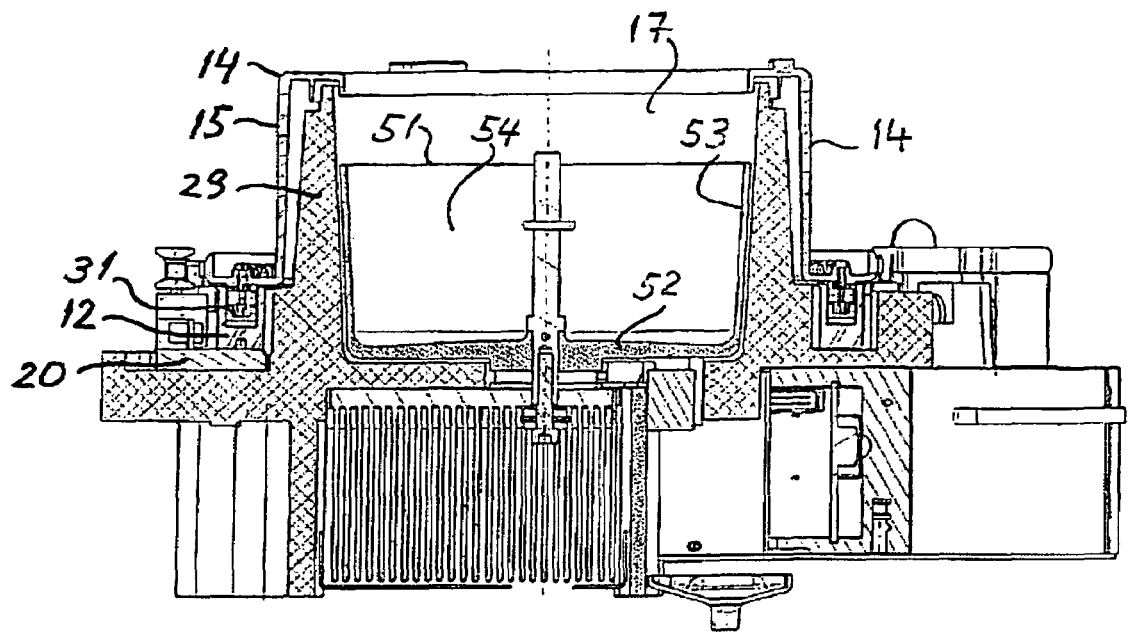
FIG. 13 shows a cross-sectional view taken along a plane H-H in FIG. 13.
Figure 12:
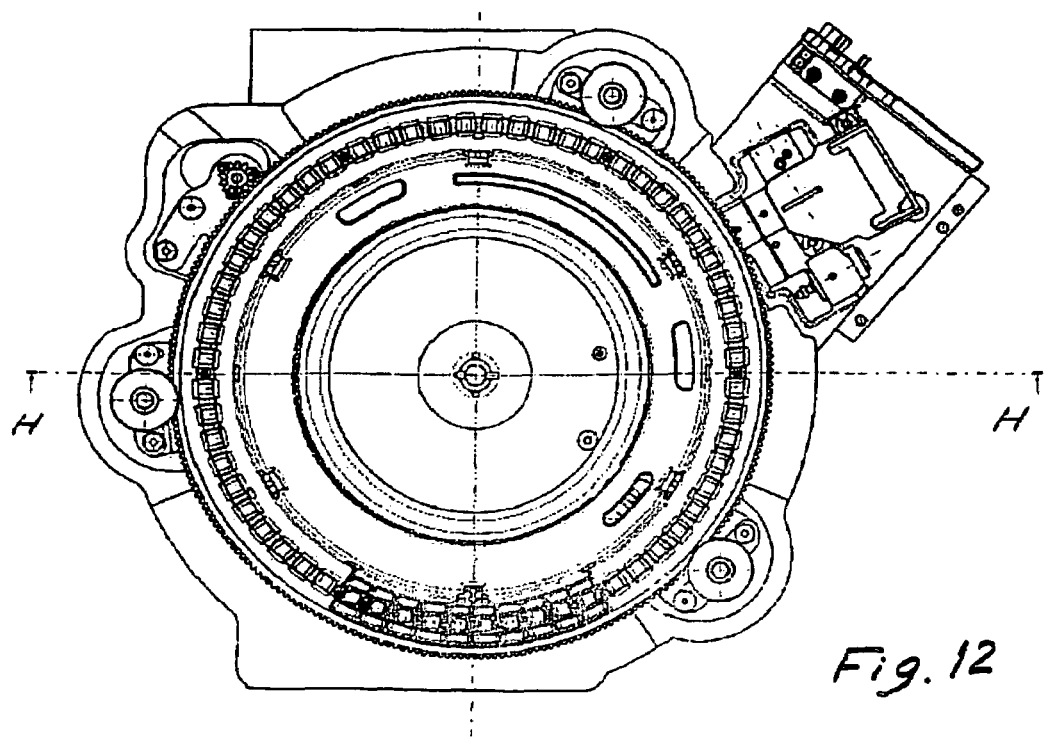
FIG. 12 shows a top view of the conveyor part of the analyzer shown in FIG. 1 when reagent container assembly 61 is removed therefrom.

FIG. 12 shows a top view of the conveyor part of the analyzer shown in FIG. 1 when reagent container assembly 61 is removed therefrom. FIG. 13 shows a cross-sectional view taken along a plane H-H in FIG. 12.

As shown by FIG. 14a hollow body 51 is arranged in chamber 17 within second ring shaped body 14. Hollow body 51 has e.g. the shape of a bucket, and has a bottom wall 52 and side walls 53 which define a chamber 54.

Figure 11:
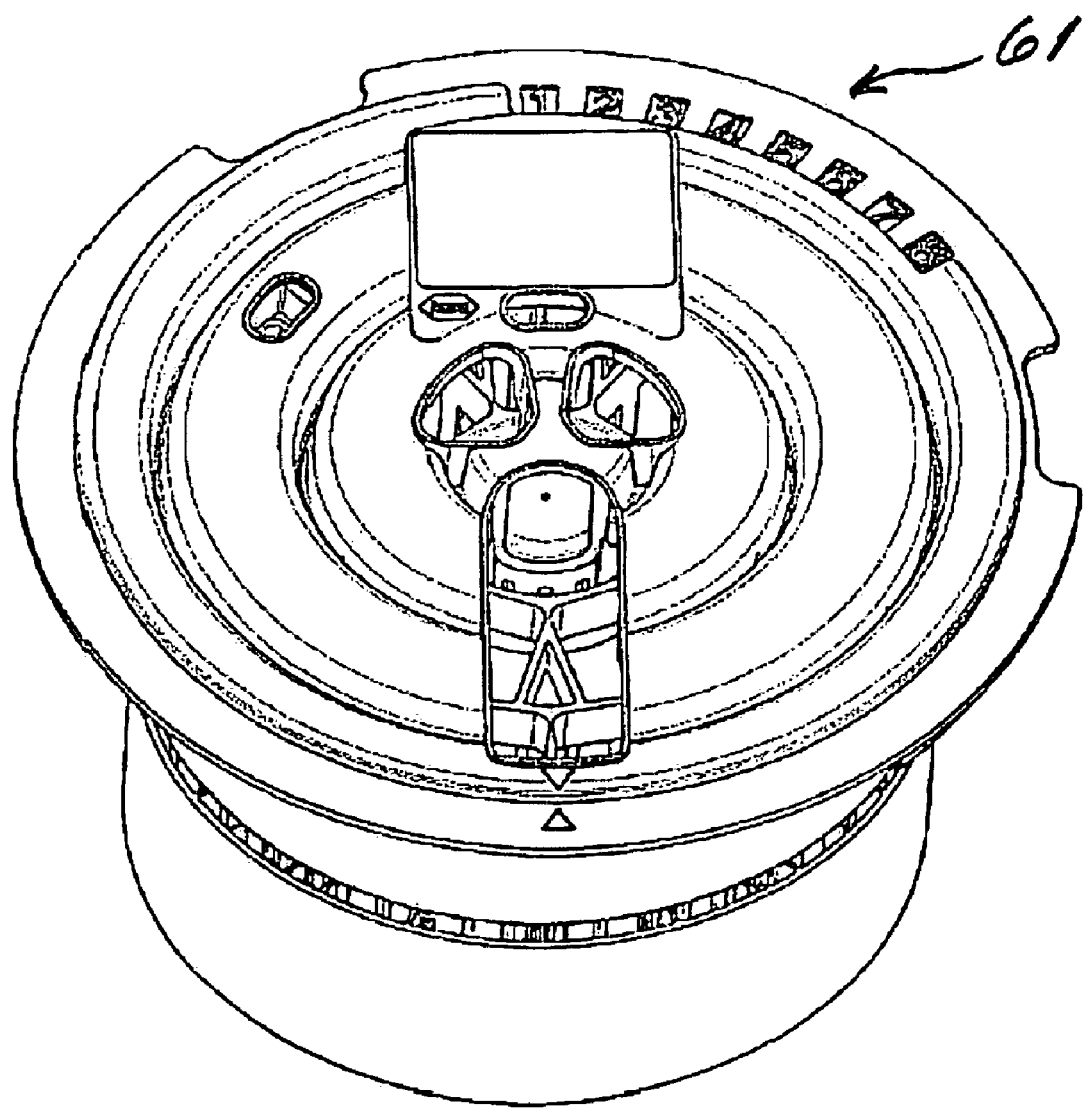
FIG. 11 shows a perspective view of reagent container assembly 61 when it is removed from the analyzer shown in FIG. 1.

FIG. 11 shows a perspective view of reagent container assembly 61 when it is removed from the analyzer shown in FIG. 1. Reagent container assembly 61 is adapted for being positioned with its lower part in chamber 54 of hollow body 51.

Figure 14:
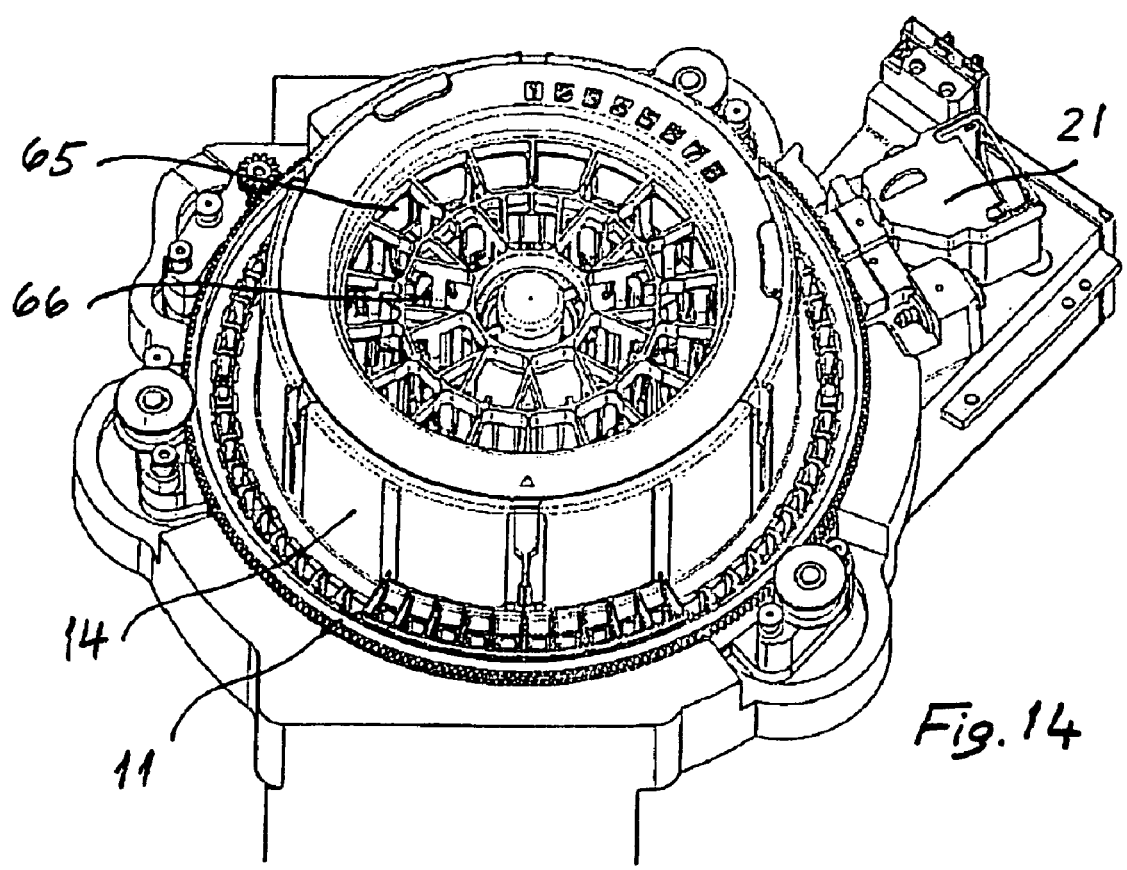
FIG. 14 shows a perspective view of reagent container assembly 61 installed in the analyzer, but without its cover and without any reagent container in it.

FIG. 14 shows a perspective view of reagent container assembly 61 installed in the analyzer, but without its cover and without any reagent container in it. FIG. 15 shows an enlarged view of a portion of FIG. 14. As can be appreciated from FIGS. 16 and 17 reagent container assembly 61 comprises a housing having two concentric arrays of chambers adapted for receiving reagent containers.

Figure 16:
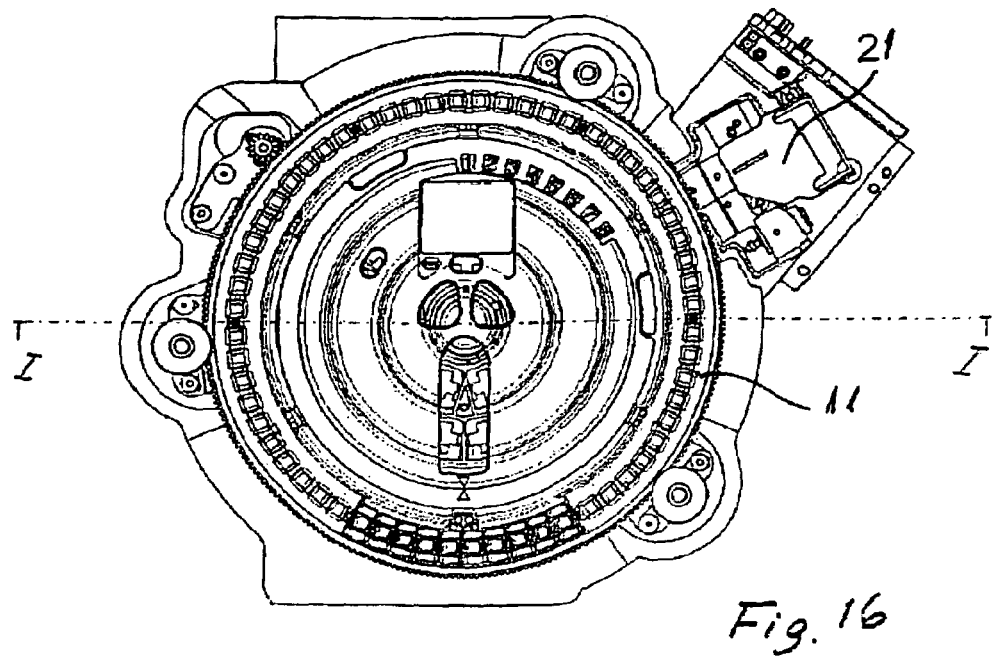
FIG. 16 shows a top view of the conveyor part of the analyzer shown in FIG. 1 and in particular reagent container assembly 61 before it is loaded with reagent containers.

FIG. 16 shows a top view of the conveyor part of the analyzer shown in FIG. 1 and in particular of reagent container assembly 61 before it is loaded with reagent containers.

FIG. 17 shows a perspective view of a reagent container 62.

FIG. 18 shows a cross-sectional view taken along a plane I-I in FIG. 16.

As shown by FIG. 18, reagent container assembly 61 contains a plurality of chambers 65, 66 for receiving reagent containers 63, 64, like reagent container 62 in FIG. 18, each of which contains a specific reagent in liquid form. Each reagent container carries an automatically readable label (not shown), e.g. a barcode label, which identifies the specific reagent contained in the reagent container.

Sample tube area 18 comprises a rack permanently installed in the analyzer. This rack has several cavities 19 and each of these cavities is adapted for receiving a sample tube containing a liquid sample to be analyzed.

Automatic pipetting unit 71 is suitable for effecting all pipetting operations in the analyzer, e.g. the pipetting of a sample portion taken from a sample tube in the sample area 18 into a reaction cuvette 31 in conveyor 11 and the pipetting of a reagent volume taken from a reagent container 62 in reagent assembly 61 into a reaction cuvette 31 in conveyor 11. After these pipetting operations the reaction cuvette contains a sample-reagent-mixture.

Automatic pipetting unit 71 comprises a removably mounted pipetting needle 72 and a transport device mounted on a rail 73 which extends in the X-direction shown in FIG. 1. This transport device moves the pipetting needle 72 in two ways: along a rectilinear path in the X-direction, e.g. for bringing pipetting needle 72 to a pipetting position, and along a circular path, e.g. when the tip of pipetting needle 72 is immersed in a liquid contained in a reaction cuvette. The latter circular movement of the pipetting needle 72 is achieved by means of an excenter mechanism which is part of the above-mentioned transport device of pipetting needle 72. The excenter mechanism is adapted for moving the tip of pipetting needle along a circular path, but keeping the length axis of pipetting needle 72 in the Z-direction shown in FIG. 1. This circular motion of the pipetting needle is used e.g. for mixing in a reaction cuvette 31 a liquid sample and a reagent which have been pipetted into the reaction cuvette. For this mixing purpose the circular motion of pipetting needle 72 is effected with the tip of pipetting needle 72 partially immersed in the sample-reagent-mixture contained in a reaction cuvette 31.

The above described excenter mechanism includes a light barrier device for roughly adjusting the initial position of the excenter mechanism so that the needle 72 has a defined initial position e.g. at its 12 o'clock position in the circular path defined by the excenter mechanism.

FIG. 19 shows a cross-sectional view of a reaction cuvette 31 inserted in a cavity 13 of conveyor 11 and of a pipetting needle 72 positioned therein.

As shown by FIGS. 1, 13, 15, 17, 23, photometer 21 is located adjacent to conveyor 11 for carrying out photometric measurements of liquid sample-reagent-mixtures contained in reaction cuvettes 31. For this purpose the driving means 22 of conveyor 11 rotate the conveyor step-wise for accurately positioning each reaction cuvette 31 in the optical path 24 of the light beam of photometer 21 so that the latter light beam passes through the center of the lower part of the cuvette which contains the sample-reagent-mixture to be measured with photometer.

Conveyor driving means comprise means for rotating conveyor 11 in a step-wise manner. Conveyor driving means comprise e.g. a belt-drive (not shown) which drives a tooth-wheel 22 of conveyor 11 and other suitable means for positioning conveyor 11 in accurate angular positions suitable for performing accurate photometrical measurements of the sample-reagent mixture contained in each of the reaction cuvettes 31.

The analyzer shown in FIG. 1 also comprises electrical and electronic components as well as hardware and software for controlling the operation of the analyzer and all components thereof whose operation has to be controlled and coordinated, e.g. the operation of the automatic pipetting unit 71, the photometer 21, the management of the samples and reagents present in the analyzer, and the evaluation and display of analysis results and related information.

A preferred embodiment of the analyzer shown in FIG. 1 comprises means for carrying out an initialization method described hereinafter for determining a reference position for the pipetting needle 72 and for positioning the pipetting needle 72 in said reference position at each start of the operation of the analyzer.

Example of a Reaction Cuvette

Figure 8:
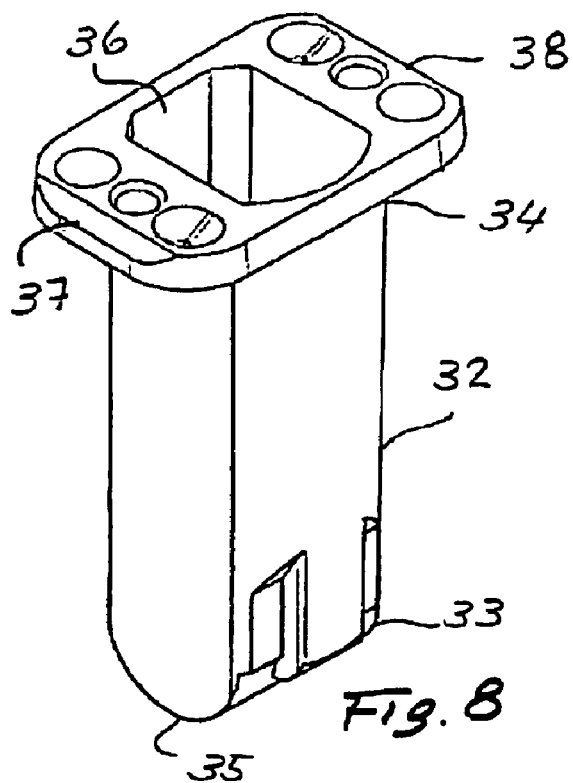
FIG. 8 shows a perspective view of a reaction cuvette 31 of the type which is preferably used with a cuvette holder 41 according to the invention.
Figure 9:
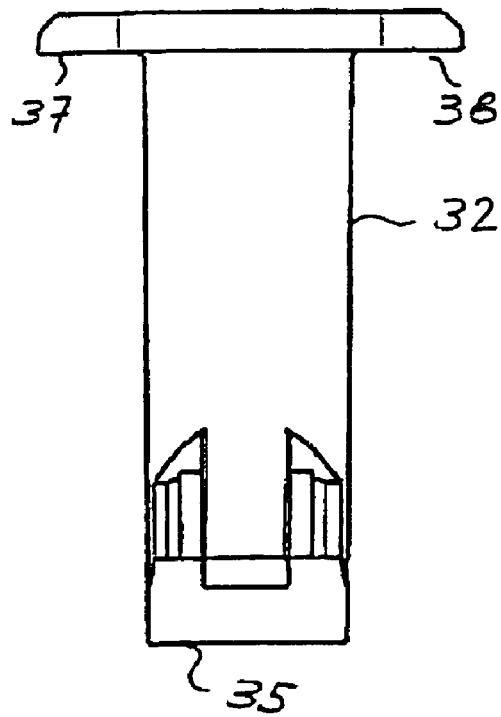
FIG. 9 shows a first side view of reaction cuvette 31 in FIG. 8.
Figure 10:
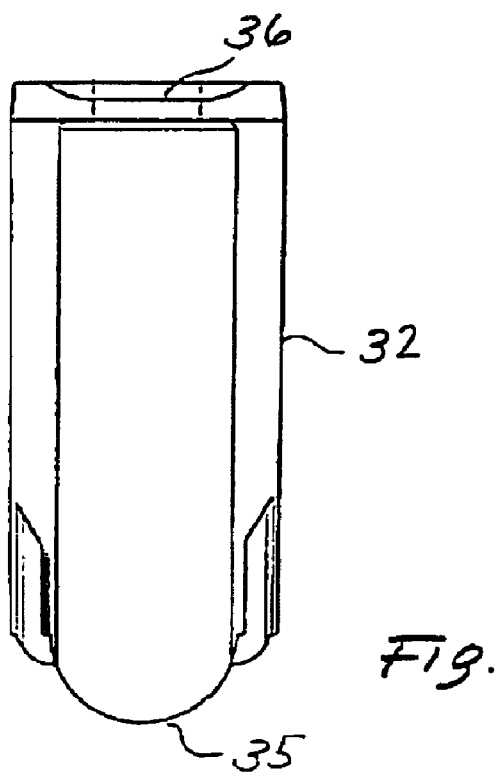
FIG. 10 shows a second side view of reaction cuvette 31 in FIG. 8.

FIG. 8 shows a perspective view of a reaction cuvette 31 of the type which is preferably used with an analyzer of the type described above. FIG. 9 shows a first side view of reaction cuvette 31 in FIG. 8. FIG. 10 shows a second side view of reaction cuvette 31 in FIG. 8. Reaction cuvette 31 is a single-piece, disposable component made by injection molding of a plastic material which is suitable for performing photometric measurements of a sample-reagent mixture contained in reaction cuvette 31.

When a reaction cuvette 31 is inserted in a cavity of conveyor 11 it is in vertical position.

As shown by FIGS. 8 to 10, reaction cuvette 31 has a rectilinear tubular body 32 which extends between a lower end portion 33 and an upper end portion 34 which lie at opposite ends of tubular body 32. Lower end portion 33 is closed by a bottom wall 35. Upper end portion 34 ends in an opening 36 and includes two tongue members 37, 38 adjacent to opening 36 of upper end portion 34. Tongue members 37, 38 extend outwardly from second end portion 34 of the tubular body 32 in opposite directions. Reaction cuvette 31 has a length symmetry axis 39.

Example of a Cuvette Array

An embodiment of a cuvette array suitable for use in an analyzer of the type described above is described hereinafter with reference to FIGS. 4-7.

FIG. 4 shows a perspective view of a cuvette array according to the invention comprising a cuvette holder 41 and a plurality of cuvettes 31 of the type described above with reference to FIGS. 8-10. FIG. 5 shows a top plan view of the cuvette array shown in FIG. 4. FIG. 6 shows a cross-sectional view taken along a plane C-C in FIG. 5 of a chamber of cuvette holder 41 and of a cuvette 31 held by that chamber. FIG. 7 shows a cross-sectional view taken along a plane D-D in FIG. 5 of a chamber of cuvette holder 41 and of a cuvette 31 held by that chamber.

As can be appreciated in particular from FIG. 4, a cuvette array according to the invention comprises a cuvette holder 41 of the above described type and a plurality of reaction cuvettes 31 of the above described type.

Cuvette holder 41 is configured and dimensioned for loosely holding a plurality reaction cuvettes 31 of the type described above with reference to FIGS. 8 to 10.

Cuvette holder 41 has a body 42 made by injection molding of a plastic material. Body 42 extends along a circular segment and defines an array of chambers 43 arranged along a circular segment. Each of chambers 43 is adapted for receiving and loosely holding the upper end portion 34 of a reaction cuvette 31 and the tongue members 37, 38 of that end portion.

The body 42 of cuvette holder 41 is an integrally made, single-piece, disposable component made by injection molding of a suitable plastic material. Body 42 comprises the following portions:
 an upper frame 45,
 a lower frame 46,
 side walls 47, 48 each of which connect an end of upper frame 45 with one end of lower frame 46,
 a plurality of intermediate walls 49 which separate neighboring chambers 43 from each other, and
 flexible tongues 40, 50 which extend downwards from the upper frame 45 and which are inclined with respect to a vertical axis passing through the center of a chamber 43.

Each of intermediate walls 49 is radially oriented, i.e. it lies in a plane that passes through the rotation axis 25 of conveyor 11, and connects upper frame 45 with lower frame 46.

The shape and dimensions of frame portions 45 and 46 are such that the array of chambers 43 of cuvette holder 41 closely corresponds to the array of cavities 13 of conveyor 11.

The space available for the upper end portion 34 of a reaction cuvette 31 in each chamber 43 of cuvette holder 41 is delimited by intermediate walls 49 which are the side walls of each chamber 43 and by flexible tongues 40 and 50 which allow the insertion of the reaction cuvette through the upper opening of the chamber, but which prevent removal of the cuvette once the upper end thereof is introduced in chamber 43.

The size of the space available for the upper end portion 34 of a reaction cuvette 31 in each chamber 43 of cuvette holder 41 is chosen large enough to allow displacement of the upper end portion 34 of reaction cuvette in X-, Y-, and Z-direction within chamber 43 and within limits determined by the size of chamber 43. The upper end portion 34 of reaction cuvette 31 and thereby the entire cuvette 31 is thus free to rotate around its length axis 31 within angular limits determined by the size of chamber 43.

In a preferred embodiment, body 42 of cuvette holder 41 further includes a connecting part 44 adapted for connecting body 42 of cuvette holder 41 to conveyor 11 of the analyzer shown in FIG. 1.

As can be appreciated in particular from FIG. 6, the space available for the upper end portion 34 of a reaction cuvette 31 in a chamber 43 of cuvette holder 41 is delimited by intermediate walls 49 which are the side walls of chamber 43 and by flexible tongues 40 and 50 which allow the insertion of the reaction cuvette through the upper opening of chamber 43, but which prevent removal of the cuvette once the upper end portion of the cuvette is introduced into chamber 43.

During the insertion of cuvettes 31 in respective cavities 13 of conveyor 11, are loosely held by cuvette holder 41, but this holder exerts no force or influence on the position each cuvette takes in a cavity 13. The own weight of each cuvette 31 is the only force that acts on it as it is inserted into a cavity 13. The accurate and defined positioning of cuvette 31 in cavity 13 is essentially determined by edges 58 and 59 of the inner surface of bottom wall 56 of cavity 13 and the close match of shape and dimensions of cuvette 31 and the cavity 13.

Example of a Needle Transport Device, which is Part of Automatic Pipetting Unit 71

As already described above, the analyzer shown by FIG. 1 comprises a rotatable conveyor 11 for conveying reaction cuvettes 12 along a circular path, conveyor driving means 22 for rotating said conveyor in a step-wise manner, an automatic pipetting unit 71 having a pipetting needle 72 for pipetting samples and reagents into the reaction cuvettes 31, thereby forming liquid sample-reagent-mixtures.

Automatic pipetting unit 71 comprises a needle transport head 74 which is moved along rail 73 in FIG. 1 for moving pipetting needle 72 along a straight line in a first direction, e.g. in a direction parallel to the X-axis in FIG. 1, to a plurality of pipetting positions all of which have centers that lie in one and the same vertical plane, e.g. a plane which is parallel to the X-Z-plane in FIG. 1, and which passes through said straight line.

Figure 20:
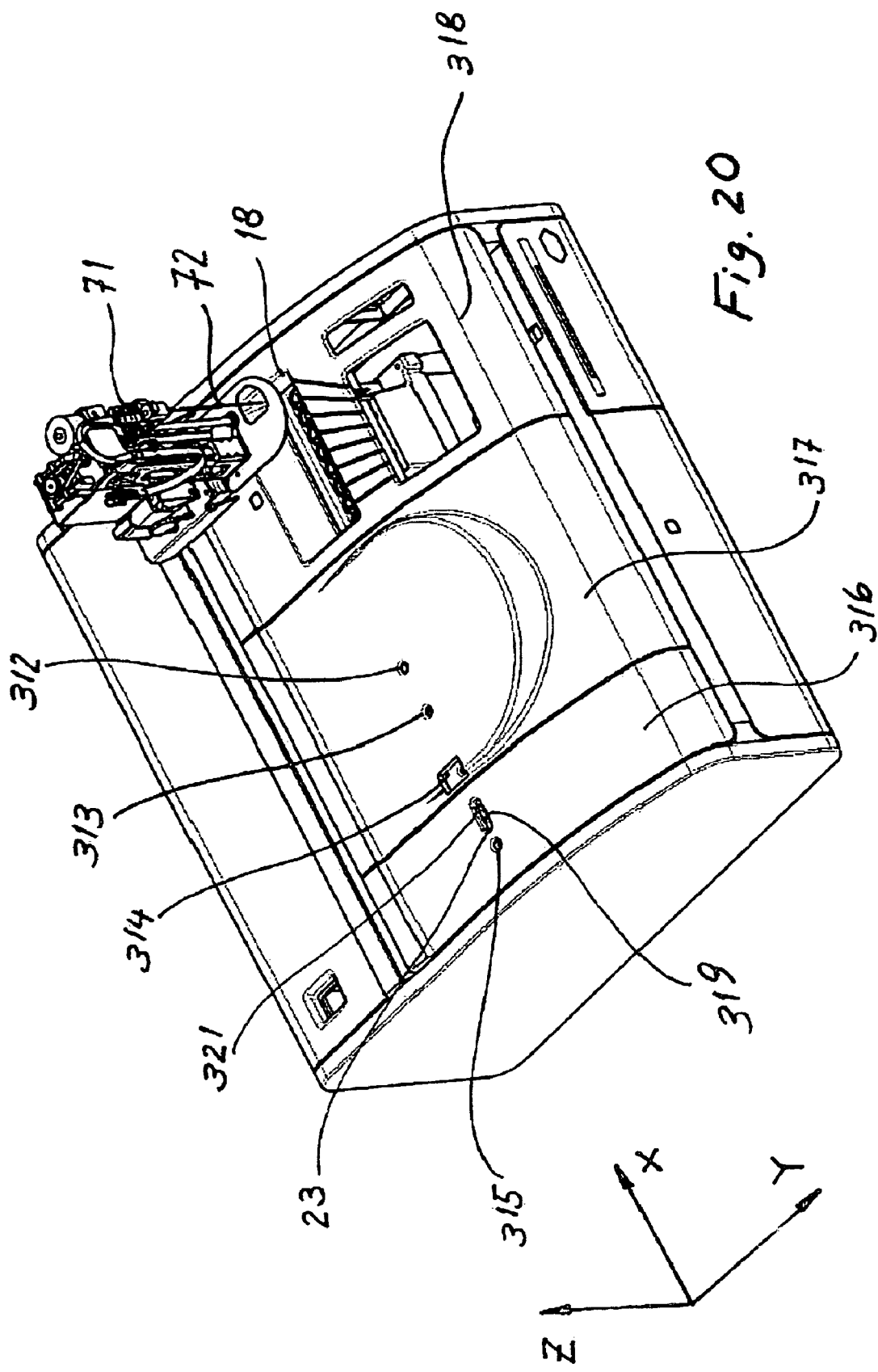
FIG. 20 shows a perspective view of the analyzer of FIG. 1 including a cover 311 with openings through which pipetting operations are performed with pipetting needle 72.

The location of the above-mentioned pipetting positions is illustrated by FIG. 20 which shows a perspective view of the analyzer of FIG. 1 including a cover composed of three cover parts 316, 317, 318. These cover parts have the following openings for performing pipetting operations with pipetting needle 72: a first opening 312 for taking a reagent volume from a reagent container, a second opening 313 for taking a reagent volume from a reagent container, a third opening 314 for performing pipetting operations in one of the reaction cuvettes on conveyor 11, a fourth opening 319 for contacting a reference member 321 for the initialization method and for accessing washing station 23 and a fifth opening 315 for performing pipetting operations in a chamber of an ISE device.

The centers of the above mentioned openings in cover parts 316, 317, 318 define the location of pipetting positions to which pipetting needle 72 has to be brought to by transport head 74.

Figure 21:
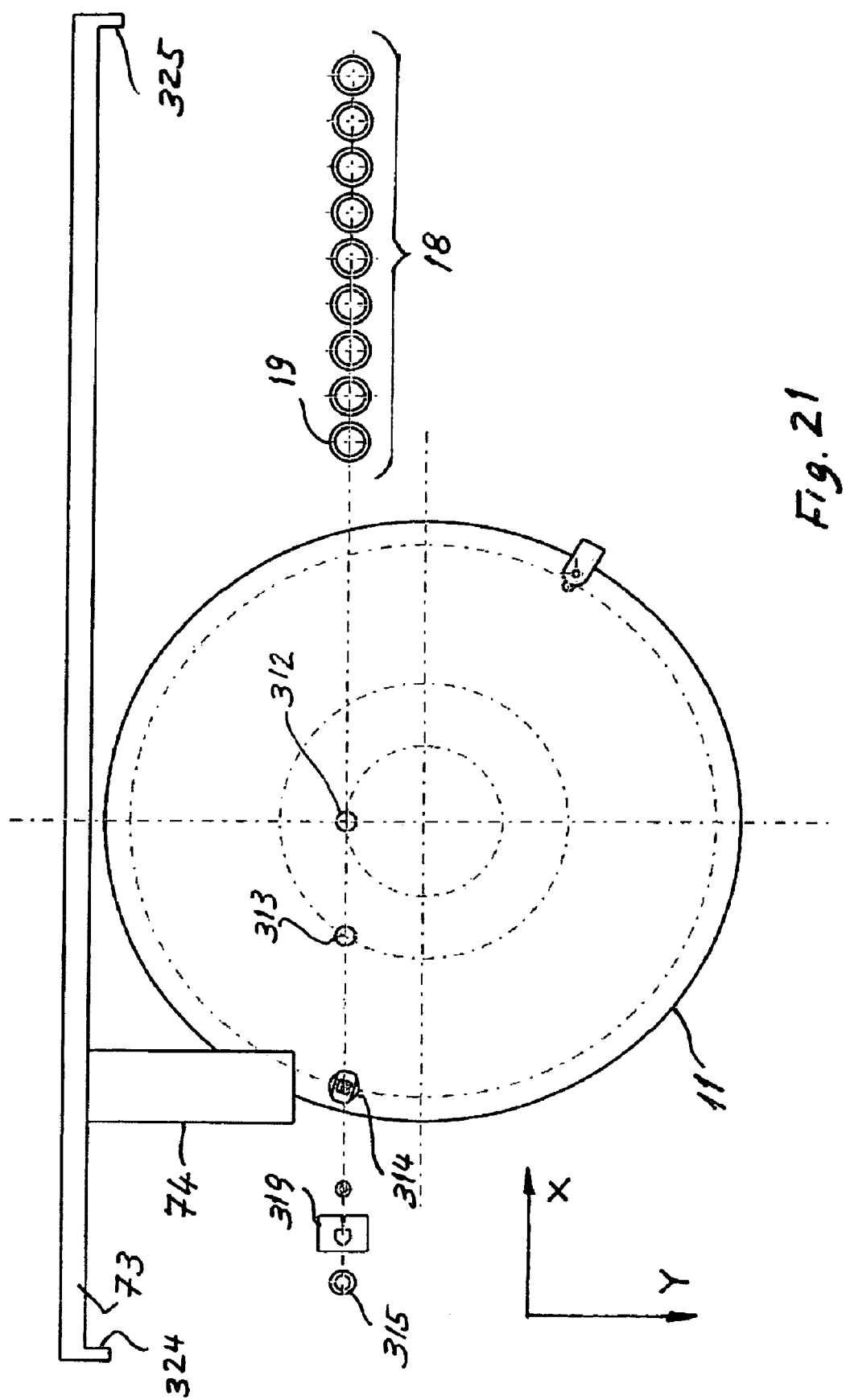
FIG. 21 shows a schematic top view of the analyzer and in particular the arrangement of the pipetting openings.

The above mentioned openings in cover parts 316, 317, 318 are also shown by the top plan view represented in FIG. 21. This Figure also shows on the right side the sample area 18 and the upper openings of cavities 19 each of which is adapted for receiving a sample tube. The centers of the openings of cavities 19 are further pipetting positions to which pipetting needle 72 has to be brought to by transport head 74.

As shown by FIGS. 20 and 21 all above-mentioned pipetting positions have centers which lie in one and the same vertical plane, which is parallel to the X-Z-plane and which passes through the straight line in X-direction along which pipetting needle 72 is moved by transport head 74. In FIG. 21 the plane where all the centers of the pipetting positions lie is represented by straight line which is called pipetting axis 320 for the purpose of this description.

Needle transport head 74 comprises an excenter mechanism for moving pipetting needle 74 along a circular path and keeping the length axis of needle 72 parallel to a vertical axis, e.g. parallel to the Z-axis in FIG. 1.

Figure 22:
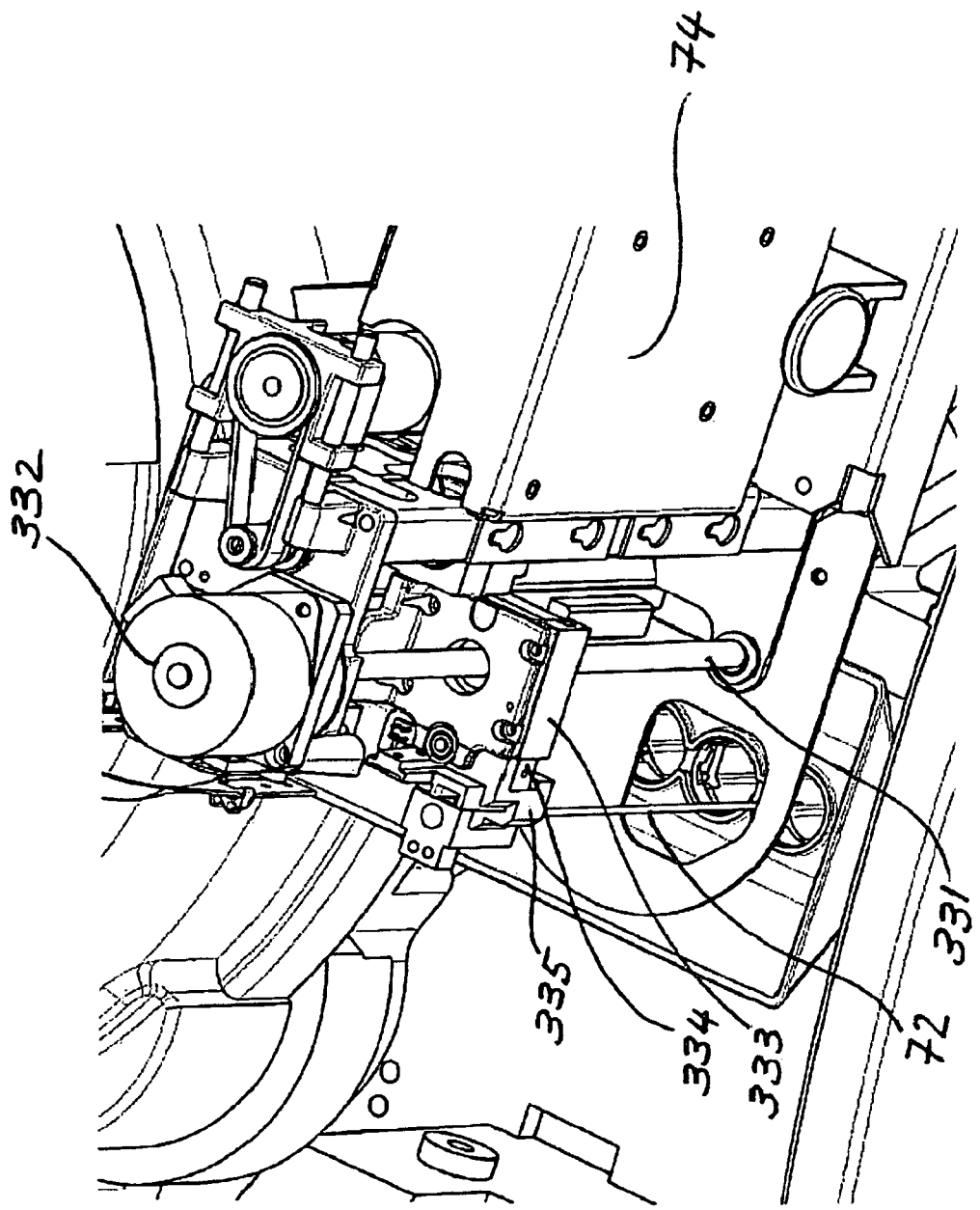
FIG. 22 shows a perspective view of the structure which holds pipetting needle 72 and moves it along a circular path for mixing liquid contained in a reaction cuvette.

FIG. 22 shows a perspective view of the structure of transport head 74 which holds pipetting needle 72 and moves it along a circular path for mixing liquid contained in a reaction cuvette 31. As shown by FIG. 22 transport head 74 comprises an excenter shaft 331 driven by a motor 332 with shaft 331 and motor 332 mounted on a frame part, and a connecting plate 334 which slides within a guide 33. Pipetting needle 72 is connected by a connecting piece 335 to an end part of connecting plate 334.

FIG. 23 schematically shows a perspective view of the structure shown in FIG. 22. FIG. 23 shows that the upper plate of guide 333 has an elongated opening 336.

FIG. 24 shows a schematic partial cross-sectional view of the structure shown by FIG. 23. FIG. 24 shows a ball bearing pin 337 which is connected to connecting plate 334 and which is adapted for sliding along opening 336.

FIG. 25 shows a cross-sectional view of the structure shown by FIG. 23.

Figure 26:
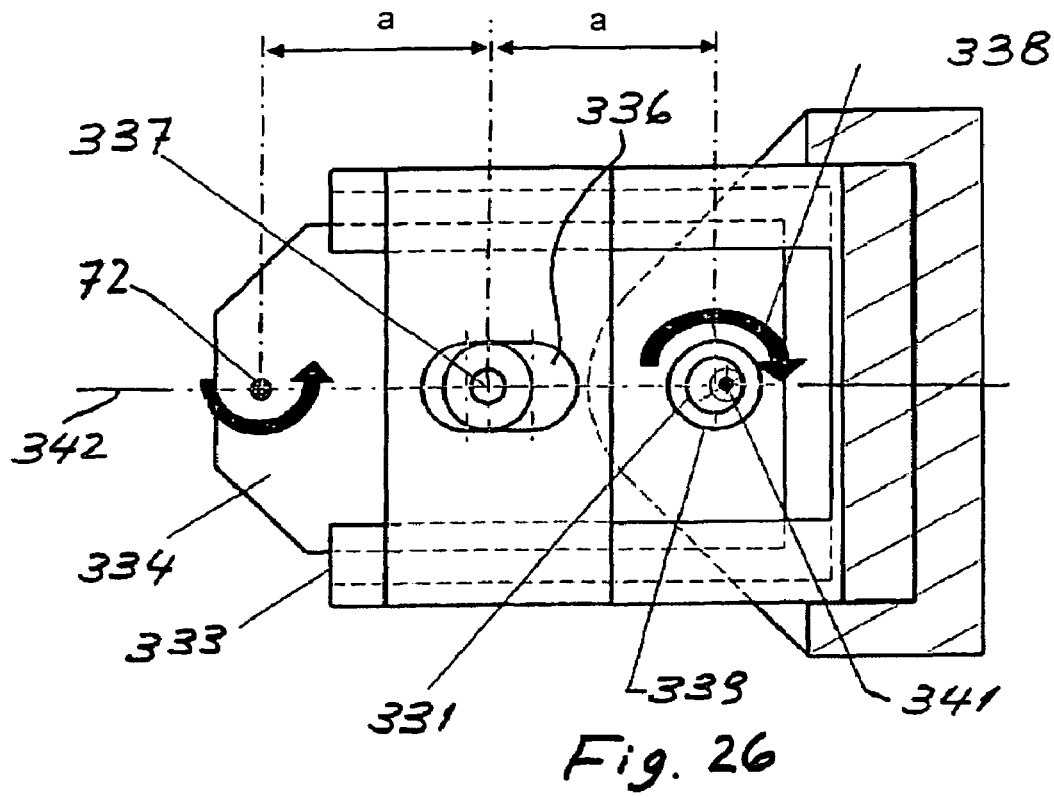
FIG. 26 shows a schematic top view of the structure shown by FIG. 23 with connecting plate 334 in a first position, with pipetting needle on the symmetry axis 342 of guide 333.

FIG. 26 shows a schematic top view of the structure shown by FIG. 23 with connecting plate 334 in a first position, with pipetting needle on the symmetry axis 342 of guide 333. FIG. 26 shows that rotation of excenter shaft 331 in the sense indicated by a curved arrow 343 causes movement of pipetting needle 72 along a circular path in the opposite sense indicated by a curved arrow 344.

FIG. 27 shows a schematic top view of the structure shown by FIG. 23 connecting plate 334 in a second position, with pipetting needle outside of the symmetry axis 342 of guide 333.

Needle transport head 74 cooperates with a level detection device (not shown) which is part of the analytical apparatus shown in FIG. 1. This level detection device is used for detecting contact of pipetting needle 72 with a liquid surface in a vessel or with a metallic part of the apparatus.

Example of a Method for Initializing the Needle Transport Device of Automatic Pipetting Unit 71

A method for initializing the needle transport device 74 of automatic pipetting unit 71 of the analyzer shown by FIG. 1 is described hereinafter with reference to FIGS. 28 to 41. This initializing method is carried out automatically immediately after each start of the analyzer.

A reference position for pipetting needle 72 is determined with the method described below for initializing the needle transport device 74 of automatic pipetting unit 71 immediately after each start of the analyzer.

For the purpose of the above mentioned initialization a reference member 321 shown in FIG. 1 is mounted at a well and accurately defined position in the analyzer.

FIG. 28 shows a top plan view of reference member 321. Reference member 321 is a small metallic plate which has the shape shown by FIG. 28 and a thickness of about 5 to 10 mm.

Reference member 321 has on one side an opening 322 which is used as a reference position for a mechanical adjustment of the position of pipetting needle when the analyzer shown in FIG. 1 is assembled at a factory. For this purpose, pipetting needle 72 is manually led to enter into opening 322 as shown by FIG. 29 and with needle 72 in this position all related mechanical parts are fixed e.g. with screws at their definitive position in the analyzer. This adjustment is not repeated during normal use of the analyzer.

For the purpose of the initialization method described below which is repeated at each start of the analyzer operation, reference member 321 has an opening 323 shown by FIG. 28.

As shown by the top plan view of FIG. 28, opening 323 has e.g. the shape of a pentagon ABCDE and comprises a rectangular zone ABCE and triangular zone CDE which have a common symmetry axis 328 which coincides with pipetting axis 320. Points M and N lie on symmetry axis 328. Triangular zone CDE is an isosceles right triangle and is composed of two isosceles right triangles DNE and DNC.

Opening 323 has an inner side surface 345 which corresponds to segment AB in FIG. 28 and which is perpendicular to symmetry axis 328. One half 346 (segment AM in FIG. 28) of side surface 345 lies on one side of symmetry axis 328, and the other half 347 (segment MB in FIG. 28) of side surface 345 lies on the opposite side of symmetry axis 328.

Opening 323 has two inner side surfaces 348 (segment DE in FIG. 28) and 349 (segment DC in FIG. 28), each of which forms an angle of 45 degrees measured in clockwise sense with symmetry axis 328. Inner side surface 348 lies on one side of symmetry axis 328, and inner side surface 349 lies on the opposite side of symmetry axis 328. Sides 348 and 349 meet on symmetry axis 328 on point D.

Before carrying out the initialization method according to the invention for determining a reference point $(X_0, Y_0, Z_0)$ for a pipetting needle 72 of an automatic pipetting unit having a needle transport device of the above-described type, a rough adjustment of the position of the pipetting needle 72 comprises automatically driving the transport head 74 of the pipetting needle along rail 73 towards a first limit stop 324 shown in FIG. 21 to define a first limit position for the needle 72 and then driving the transport head 74 of the pipetting needle along rail 73 in the opposite sense towards a second limit stop 325 shown in FIG. 21 to define a second limit position for the needle 72 along pipetting axis. On the basis of data obtained by the determination of these limit positions, the automatically controlled transport head 74 is able to position needle 72 at certain desired positions along pipetting axis 320 for carrying out the initialization method described hereinafter. In addition, a rough adjustment of the initial position of the excenter mechanism is carried out by the above-mentioned light barrier device.

This initial rough adjustments are followed by a method according to the invention described hereinafter for determining a reference point $(X_0, Y_0, Z_0)$ for a pipetting needle 72 of an automatic pipetting unit having a needle transport device of the above-described type. This method is described with reference to FIGS. 30-37 and comprises the following steps:

(i) A first measuring step for measuring a first displacement error $\Delta X$ in a displacement of pipetting needle 72 effected by the above mentioned transport device along a straight line in a first direction (pipetting axis 320, which is e.g. parallel to the X-axis), the first error $\Delta X$ being caused by a corresponding first angular error $\phi$ of an initial angular position of the pipetting needle along the circular path determined by the excenter mechanism.

Figure 30:
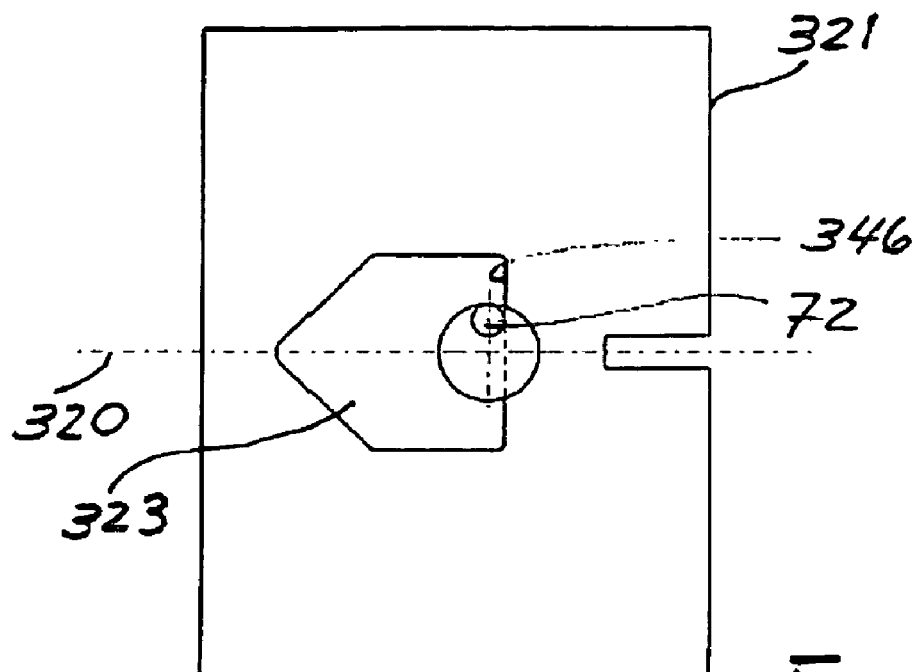
FIG. 30 illustrates a first step of a method for determining a reference, initial or home position for the pipetting needle.
Figure 31:
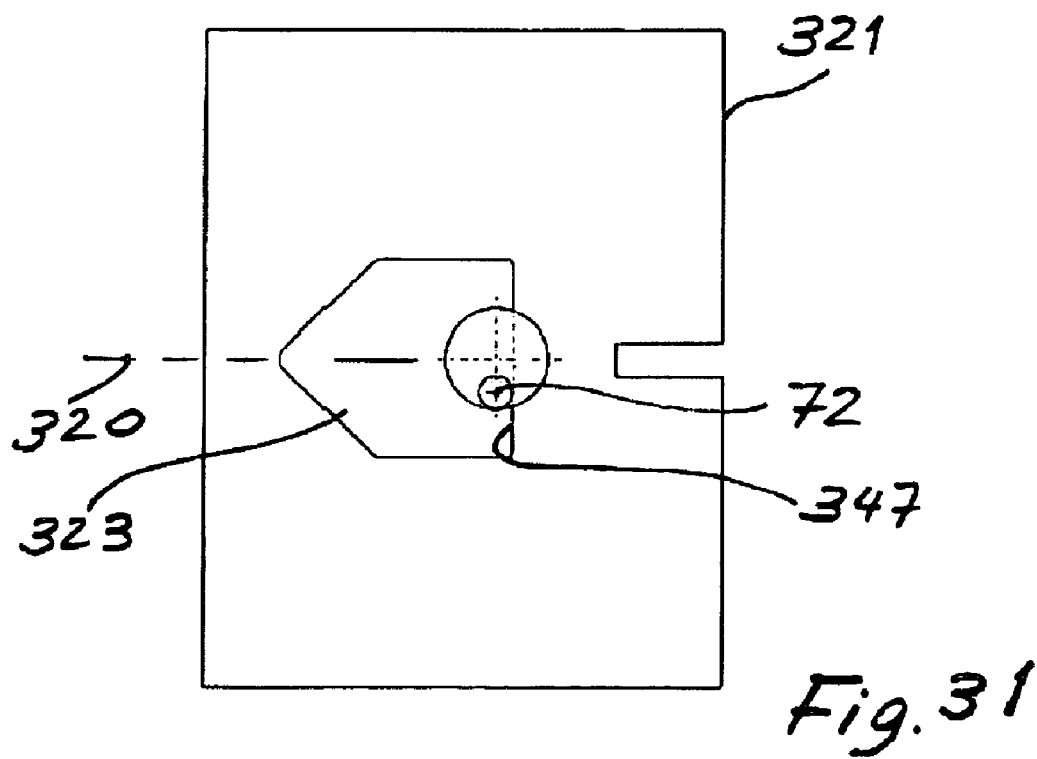
FIG. 31 illustrates a second step of the method for determining a reference, initial or home position for the pipetting needle.
Figures 35, 36, 37:
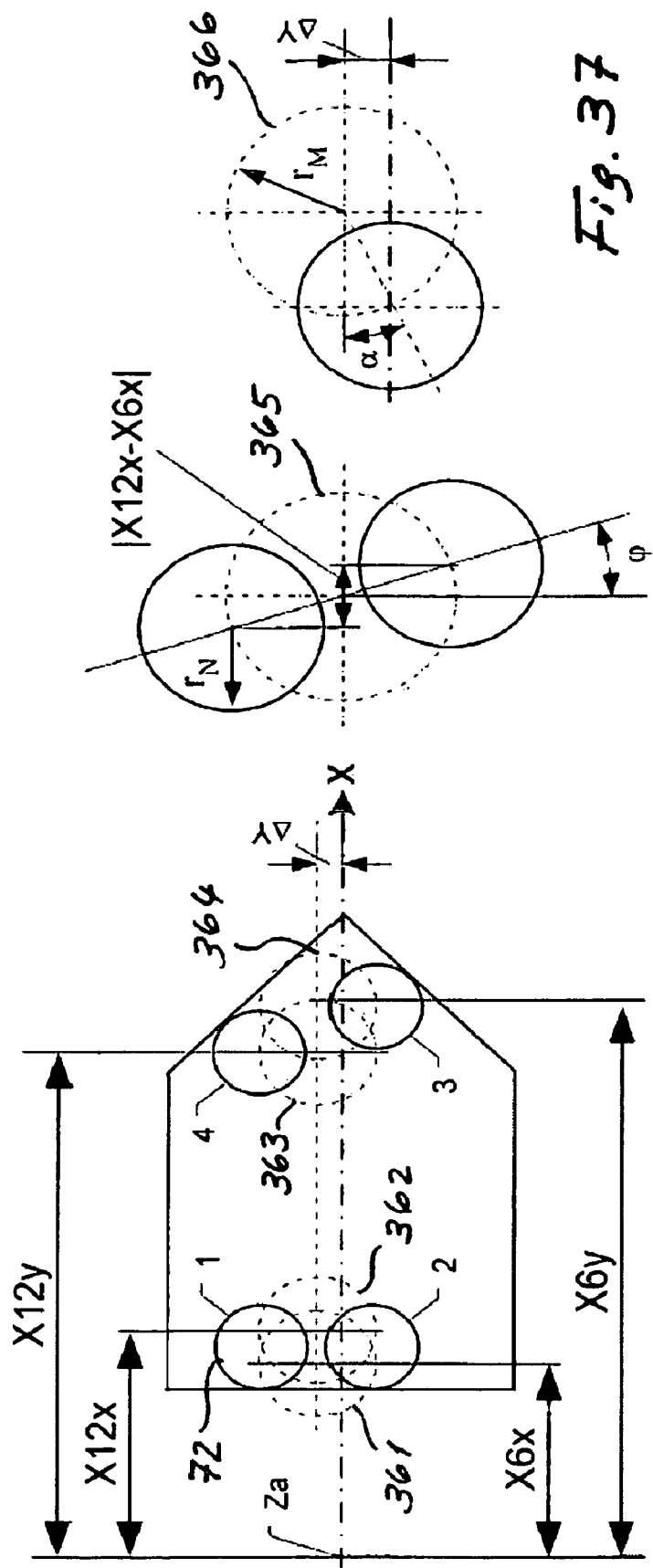
FIG. 35 is a diagram showing parameters related to the methods steps one to four illustrated by FIGS. 25 to 28.
FIG. 36 is a diagram showing parameter related to the correction of the angular position of the excenter device to compensate for an error ΔX caused by an error in the initial angular position of needle 72 due to inaccuracy in the initial position of the excenter device.
FIG. 37 is a diagram showing parameter related to the deviation of the position of the pipetting needle in Y-direction necessary after the correction of the error in the initial angular position of needle 72.

This first measuring step comprises the following steps illustrated by FIGS. 30, 31 and 35:

(1) automatically placing pipetting needle 72 on axis 320 and approximately in the center of opening 323, actuating the excenter mechanism to bring needle 72 to its 12 o'clock position shown by FIG. 30, and displacing needle 72 with transport head 74 towards inner side surface 346 of opening 323 until contact is detected with the level detection means associated with needle 72 in order to determine a value X12x corresponding to the position of needle 72 when that contact is detected, and (2) automatically placing pipetting needle 72 again on axis 320 and approximately in the center of opening 323, actuating the excenter mechanism to bring needle 72 to its 6 o'clock position shown by FIG. 31, displacing needle 72 with transport head 74 towards inner side surface 347 of opening 323 until contact is detected with the level detection means associated with needle 72 in order to determine a value X6x corresponding to the position of needle 72 when the latter contact is detected.

With the values X12x and X6x measured in step (1) respectively step (2) the above mentioned displacement error $\Delta X$ is calculated by the formula $$\Delta X = X12x - X6x$$

and the above mentioned error $\phi$ of the initial angular position of pipetting needle 72 is calculated by the following formula:

$$\varphi = \arcsin\left(\frac{|X12x - X6x|}{2 \cdot r_M}\right)$$

FIG. 36 is a diagram showing the parameters involved in the determination of $\Delta X$ and $\phi$. In FIG. 36, $r_N$=radius of pipetting needle 72.

The above mentioned determinations of $\Delta X$ and angular error $\phi$ are followed by (ii) A first correcting step for correcting the above mentioned displacement error $\Delta X$ by means of a corresponding correction of error $\phi$ of the initial angular position of pipetting needle 72. After this correction pipetting needle is positioned on pipetting axis 320 at a corrected position in X-direction and approximately in the center of opening 323.

The first correcting step is followed by (iii) A second measuring step for measuring a second displacement error $\Delta Y$ in a displacement of pipetting needle 72 in a second direction (Y-axis) perpendicular to the vertical plane (parallel to plane X-Z). The second displacement error $\Delta Y$ is caused by a corresponding second angular error $\alpha$ of an initial angular position of pipetting needle 72 along its circular path determined by the excenter mechanism.

Figure 32:
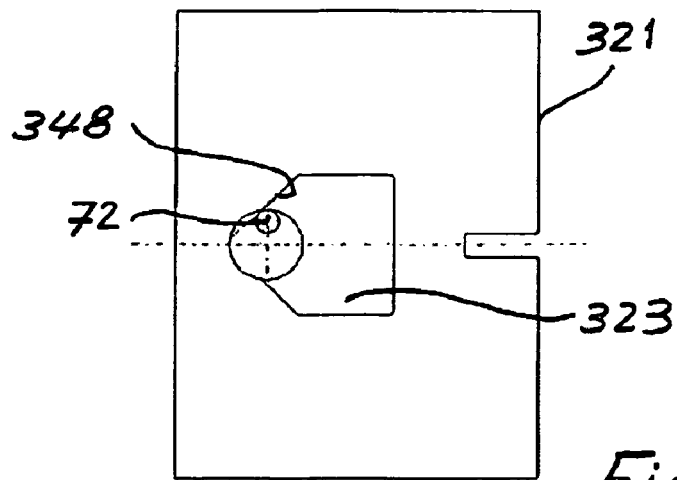
FIG. 32 illustrates a third step of the method for determining a reference, initial or home position for the pipetting needle.
Figure 33:
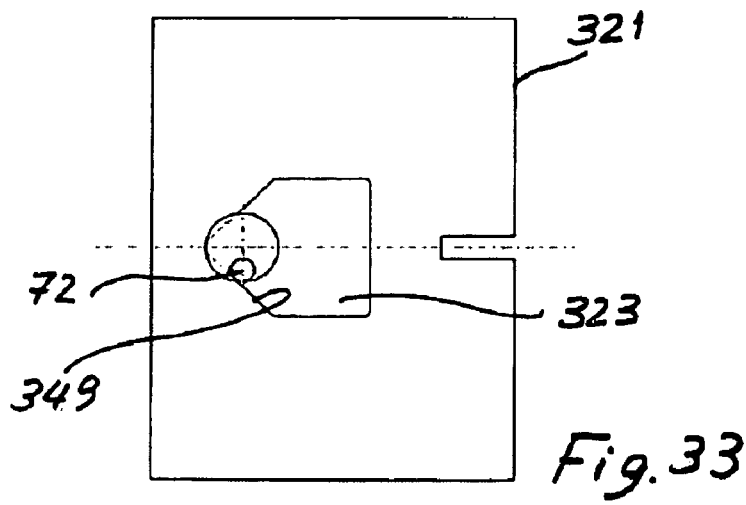
FIG. 33 illustrates a fourth step of the method for determining a reference, initial or home position for the pipetting needle.

This second measuring step comprises the following steps illustrated by FIGS. 32, 33 and 35:

(3) automatically placing pipetting needle 72 on axis 320 and approximately in the center of opening 323, actuating the excenter mechanism to bring needle 72 to its 12 o'clock position shown by FIG. 32, and displacing needle 72 with transport head 74 towards inner side surface 348 of opening 323 until contact is detected with the level detection means associated with needle 72 in order to determine a value X12y corresponding to the position of needle 72 when that contact is detected, (4) automatically placing pipetting needle 72 again on axis 320 and approximately in the center of opening 323, actuating the excenter mechanism to bring needle 72 to its 6 o'clock position shown by FIG. 33, displacing needle 72 with transport head 74 towards inner side surface 349 of opening 323 until contact is detected with the level detection means associated with needle 72 in order to determine a value X6y corresponding to the position of needle 72 when the latter contact is detected.

With the values X12y and X6y measured in step (3) respectively step (4) the above mentioned displacement error ΔY is calculated by the formula $$\Delta Y = \frac{X12y - X6y}{2}.$$

This value is negative, when ΔY lies above the X-axis in FIG. 35.

And the above mentioned error a of the initial angular position of pipetting needle 72 is calculated by the following formula:

$$\alpha = -\arcsin\left(\frac{\Delta Y}{r_M}\right)$$

with $r_M$=radius of the circular path of the pipetting needle.

FIG. 37 is a diagram showing the parameters involved in the determination of ΔY and α. In FIG. 37, $r_M$=radius of the circular path of pipetting needle 72.

Figure 39:
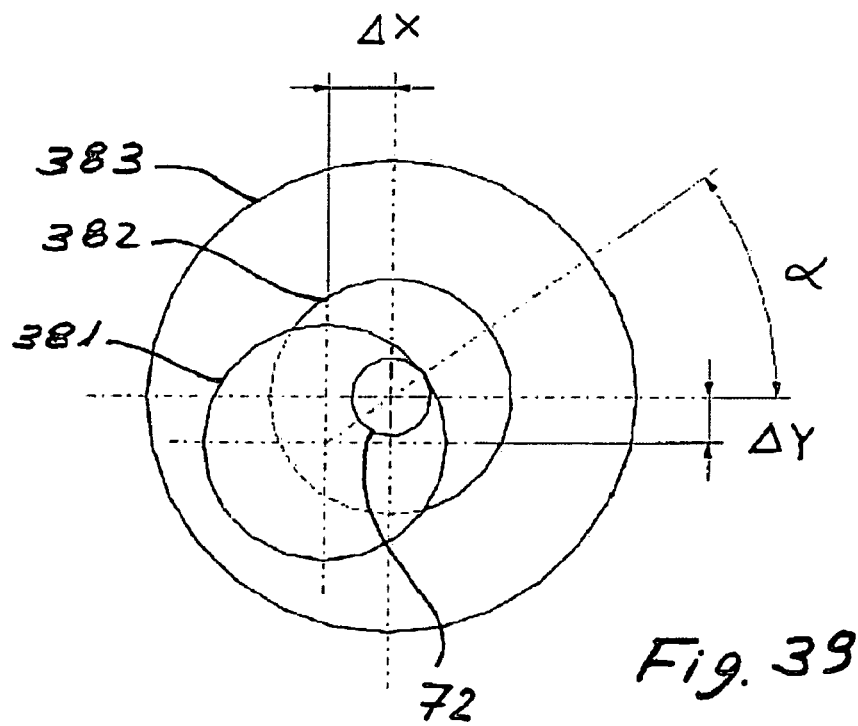
FIG. 39 is a schematic top view of the pipetting needle in the washing position and shows the deviations in X- and Y-direction of the position of the pipetting needle and the corresponding correction angle α.

FIG. 39 is a schematic top view of the pipetting needle 72 in the center of washing position 23 and shows the deviations in X- and Y-direction of the position of the pipetting needle and the corresponding correction angle α. FIG. 39 shows a schematic representation of the excenter mechanism 381 which moves needle 72 along a circular path, the inner radius 382 and the outer radius 383 of washing position 23.

The above mentioned determinations of ΔY and angular error a are followed by (iv) A second correcting step for correcting the second displacement error ΔY by means of a corresponding angular change α of the angular position of pipetting needle 72 along its circular path.

The second correcting step is followed by (v) A third measuring step for determining the position of a vertical reference line, said reference line being a line where said pipetting needle contacts a fixed first reference plane surface in the apparatus, said first plane surface lying in a plane (Y-Z) perpendicular to said straight line in said first direction (X-axis).

Figure 34:
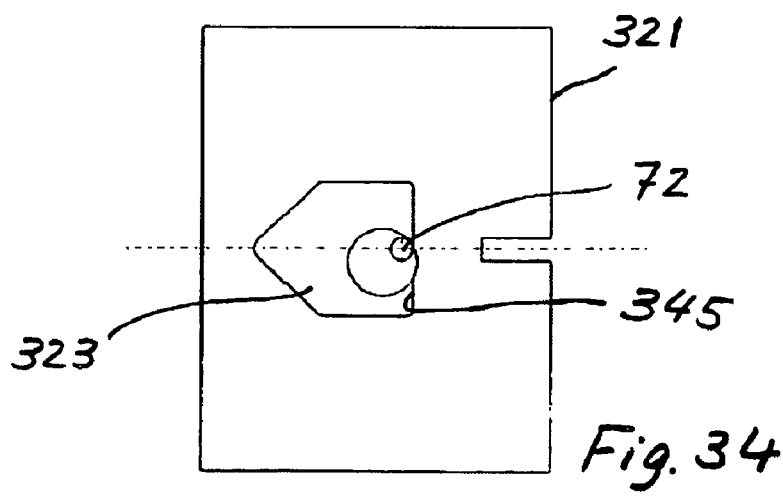
FIG. 34 illustrates a fifth step of the method for determining a reference, initial or home position for the pipetting needle.

This third measuring step comprises the following steps illustrated by FIG. 34:

(5) automatically placing pipetting needle 72 on axis 320 and approximately in the center of opening 323, actuating the excenter mechanism to bring needle 72 to its 3 o'clock position which as shown by FIG. 34 puts needle 72 in pipetting axis 320, and displacing needle 72 with transport head 74 towards inner side surface 345 of opening 323 until contact is detected with the level detection means associated with needle 72 in order to determine a reference line with coordinates $X_0$, $Y_0$ which corresponds to the position of needle 72 when the latter contact is detected.

The third measuring step is followed by (vi) A fourth measuring step for determining the position of a reference point ($X_0$, $Y_0$, $Z_0$) along the above mentioned reference line, said reference point being the point where the tip of said pipetting needle contacts a fixed second reference plane surface in the apparatus, said second reference plane surface lying in a plane (parallel to plane X-Z) perpendicular to the reference line. For determining the coordinate $Z_0$ of the reference point, it is e.g. convenient to automatically drive needle 72 towards a top horizontal surface of washing station 23 which as shown by FIG. 23 lies in the vicinity of reference member 321 and to detect contact of the tip of needle 72 with that horizontal top surface by means of the level detection device operatively associated with pipetting needle 72.

Example of a Method for Fine Adjustment of the Angular Position of the Conveyor after the Above-Described Initialization of the Needle Transport Device of Automatic Pipetting Unit 71

Figure 40:
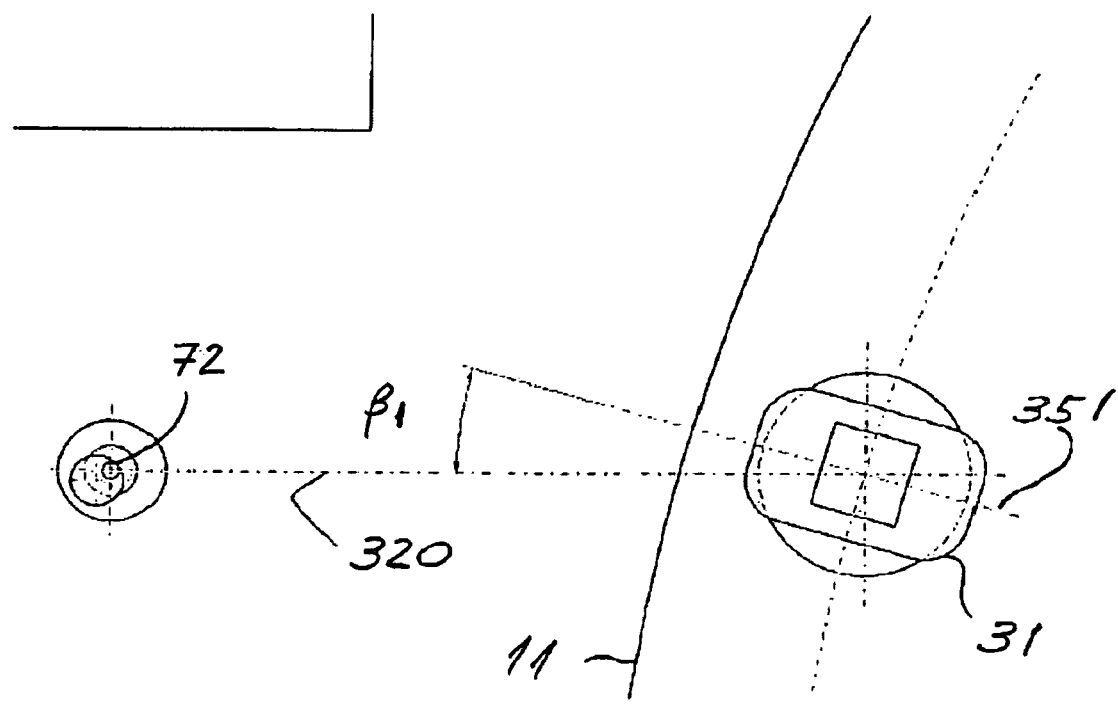
FIG. 40 is a schematic partial top view of conveyor 11 showing the theoretical angle $\beta_1$ between the linear motion path of the pipetting needle and a radius passing through the center of a reaction cuvette 31 positioned in a cavity of conveyor 11.

FIG. 40 shows the predetermined angular position $\beta_1$ of conveyor 11 for placing a reaction cuvette 31 on conveyor 11 in pipetting position 314 shown by 21. FIG. 4 shows pipetting axis 320 and axis 351 of cuvette 31.

After execution of the above described initialization process for automatically determining a reference position for pipetting needle 72, the corrections ΔX and ΔY in the position the needle 72 cause a certain deviation from of the needle from the center of a reaction cuvette positioned by step-wise rotation of conveyor 11 in pipetting position 314 shown by 21. In order to compensate for this deviation of the relative position of pipetting needle 72 with respect to reaction cuvette 31, and in line with a further aspect of the invention the predetermined angular position $\beta_1$ of conveyor 11 is corrected of an angle δ and this puts conveyor in a corrected angular position $\beta_2$.

The required value of $\beta_2$ and is calculated by the following formula δ

$$\beta_2 = \arcsin\left(\frac{a_x - \Delta Y}{r_R}\right)$$

$$\delta = \beta_2 - \beta_1$$

The correction ΔX achieved by that correction is given by the formula $$\Delta X = r_M \cdot \cos(\alpha) + r_R(\cos(\beta_1) - \cos(\beta_2))$$

Figure 38:
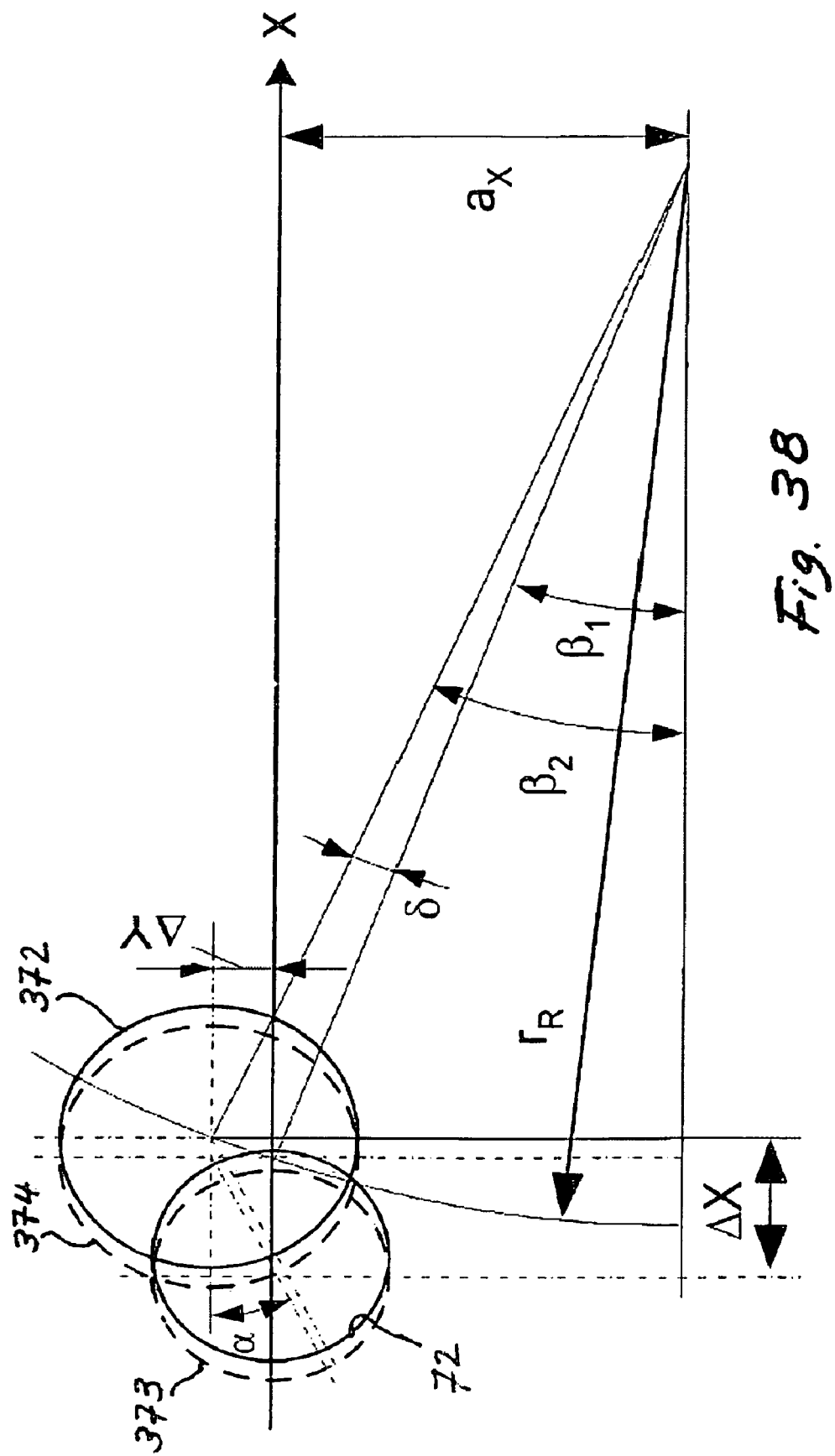
FIG. 38 is a diagram showing parameters related to the correction of the angular position of conveyor 11 to compensate for the deviations in X- and Y-direction.

FIG. 38 is a diagram showing parameters related to the calculation of $\beta_2$, the corrected angular position of conveyor 11 necessary for compensating the deviations in X- and Y-direction introduced by execution of the above described initialization method. In FIG. 38 a full circle shows the position of pipetting needle 72 before the angular position of conveyor 11 is corrected of an angle δ and circle 373 shows the position of needle after that correction. In FIG. 38 a full circle 372 shows the circular path of pipetting needle 72 before the angular position of conveyor 11 is corrected of an angle δ and circle 374 shows the circular path of pipetting needle 72 after that correction. In FIG. 38 rR represents the radius of conveyor 11.

Figure 41:
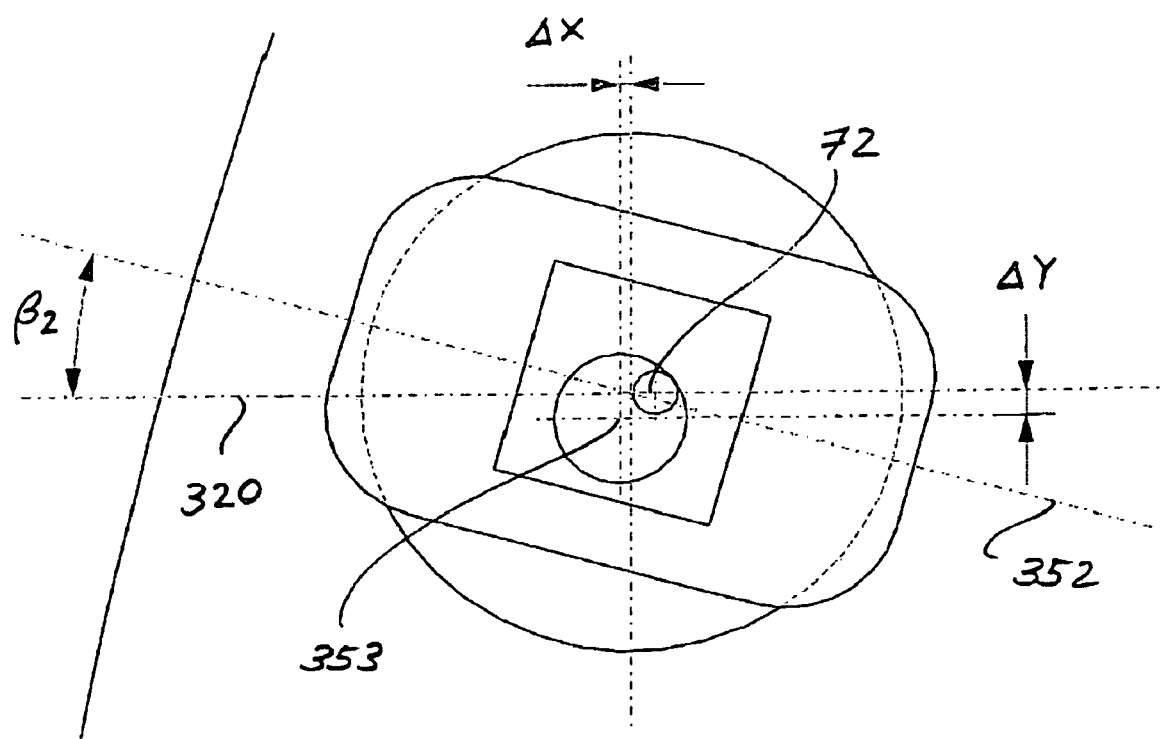
FIG. 41 is a schematic partial top view of conveyor 11 showing a corrected angle $\beta_2$ between the linear motion path of the pipetting needle and a radius passing through the center of a reaction cuvette 31 positioned in a cavity of conveyor 11.

FIG. 41 is a schematic partial top view of conveyor 11 showing a corrected angle $\beta_2$ between the linear motion path of the pipetting needle 72 along pipetting axis 320 and a radius 352 passing through the center of a reaction cuvette 31 positioned in a cavity of conveyor 11. FIG. 41 also shows the position of pipetting needle 72 with respect to cuvette 31 after the above described correction of the angular position of conveyor 11.

Although preferred embodiments of the invention have been described using specific terms, such description is for illustrative purposes only, and it is to be understood that changes and variations may be made without departing from the spirit or scope of the following claims.

What is claimed is:

1. A method for determining a reference position for a pipetting needle which is part of an automatic analytical apparatus which comprises
    a rotatable conveyor for conveying reaction cuvettes along a circular path,
    conveyor driving means for rotating said conveyor in a step-wise manner,
    an automatic pipetting unit having a pipetting needle for pipetting samples and reagents into said reaction cuvettes, thereby forming liquid sample-reagent-mixtures,
        said automatic pipetting unit having a needle transport device for moving said pipetting needle along a straight line in a first direction (X-axis) to a plurality of pipetting positions all of which have centers that lie in one and the same vertical plane (X-Z-plane) which passes through said straight line,
        said needle transport device comprising an excenter mechanism for moving said pipetting needle along a circular path and keeping the length axis of said needle parallel to a vertical axis,
    level detection means for detecting contact of said pipetting needle with a liquid surface in a vessel or with a metallic part of the apparatus, and
    a reference member for determining a reference position, said method comprising:
    (a) a first measuring step for measuring a first displacement error ($\Delta X$) in a displacement of said pipetting needle effected by said transport device along said straight line in said first direction (X-axis), said first error ($\Delta X$) being caused by a corresponding first angular error ($\phi$) of an initial angular position of said pipetting needle along said circular path determined by said excenter mechanism, said first measuring step comprising actuating the excenter mechanism of the pipette needle to bring the needle in contact with the reference member,
    (b) a first correcting step for correcting said first displacement error ($\Delta X$) by means of a corresponding correction of said angular error ($\phi$) of said initial angular position of said pipetting needle,
    (c) a second measuring step for measuring a second displacement error ($\Delta Y$) in a displacement of said pipetting needle in a second direction (Y-axis) perpendicular to said vertical plane, said second displacement error ($\Delta Y$) being caused by a corresponding second angular error ($\alpha$) of an initial angular position of said pipetting needle along said circular path determined by said excenter mechanism, said second measuring step comprising actuating the excenter mechanism of the pipette needle to bring the needle in contact with the reference member,
    (d) a second correcting step for correcting said second displacement error ($\Delta Y$) by means of a corresponding change ($\alpha$) of the angular position of said pipetting needle along said circular path,
    (e) a third measuring step for determining the position of a vertical reference line, said reference line being a line where said pipetting needle contacts a fixed first reference plane surface in the apparatus, said first plane surface lying in a plane (Y-Z) perpendicular to said straight line in said first direction (X-axis), and
    (f) a fourth measuring step for determining the position of a reference point (X0, Y0, Z0) along said reference line, said reference point being the point where the tip of said pipetting needle contacts a fixed second reference plane surface in the apparatus, said second reference plane surface lying in a plane (X-Z) perpendicular to said reference line.

2. An automatic analytical apparatus, said apparatus comprising:
    a rotatable conveyor for conveying reaction cuvettes along a circular path,
    conveyor driving means for rotating said conveyor in a step-wise manner,
    an automatic pipetting unit having a pipetting needle for pipetting samples and reagents into said reaction cuvettes, thereby forming liquid sample-reagent-mixtures,
    said automatic pipetting unit having a needle transport device for moving said pipetting needle along a straight line to a plurality of pipetting positions all of which have centers that lie in one and the same vertical plane which passes through said straight line, and
    said needle transport device comprising an excenter mechanism for moving said pipetting needle along a circular path, keeping the length axis of said needle parallel to a vertical axis,
    level detection means for detecting contact of said pipetting needle with a liquid surface in a vessel or with a metallic part of the apparatus,
    a reference member means for determining a reference position for the pipetting needle and for positioning the pipetting needle in said reference position by a method according to claim 1, and
    electronic circuit means for controlling the operation of said conveyor driving means, said needle transport device, said level detection means and said means for determining a reference position for the pipetting needle and for positioning the pipetting needle in said reference position.

* * * * *